(12) United States Patent
Wolber et al.

(10) Patent No.: US 6,461,816 B1
(45) Date of Patent: Oct. 8, 2002

(54) METHODS FOR CONTROLLING CROSS-HYBRIDIZATION IN ANALYSIS OF NUCLEIC ACID SEQUENCES

(75) Inventors: Paul K. Wolber, Los Altos; Robert H. Kincaid, Half Moon Bay, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/350,969

(22) Filed: Jul. 9, 1999

(51) Int. Cl.[7] .......................... C12Q 1/68; C12P 19/34; C07H 21/02; C07H 21/04
(52) U.S. Cl. .................. 435/6; 435/91.1; 536/23.1; 536/24.3
(58) Field of Search .................. 435/6, 91.1; 536/24.3, 536/23.1

(56) References Cited

U.S. PATENT DOCUMENTS

| | | |
|---|---|---|
| 5,434,047 A | 7/1995 | Arnold, Jr. |
| 5,585,481 A | 12/1996 | Arnold, Jr. et al. |
| 5,837,832 A | 11/1998 | Chee et al. |
| 5,858,659 A | 1/1999 | Sapolsky et al. |

OTHER PUBLICATIONS

Chee et al., "Accessing Genetic Information with High–Density DNA Arrays," Science, Oct. 25, 1996, vol. 274, pp. 610–614.*

Kafatos et al., "Determination of nucleic acid sequences homologies and relative concentrations by a dot hybridization procedure," Nucleic Acids Research, 1979, vol. 7, No. 6, pp. 1541–1552.*

L. Wodicka, et al., *Nature Biotechnology*, 15:1359–1367 (1997); "Genome–wide Expression Monoitoring in *Saccharomyces cerevisiae*".

* cited by examiner

*Primary Examiner*—John S. Brusca
*Assistant Examiner*—Young Kim

(57) ABSTRACT

Methods, reagents and kits are disclosed for selecting target-specific oligonucleotide probes, which may be used in analyzing a target nucleic acid sequence. In one aspect the present invention is directed to selecting a set of target-specific oligonucleotide probes. A cross-hybridization oligonucleotide probe is identified based on a candidate target-specific oligonucleotide probe for the target nucleic acid sequence. The cross-hybridization oligonucleotide probe measures the extent of occurrence of a cross-hybridization event having a predetermined probability. Cross-hybridization results are determined employing the cross-hybridization oligonucleotide probe and the target-specific oligonucleotide probe. The target-specific oligonucleotide probe is selected or rejected for the set based on the cross-hybridization results.

28 Claims, No Drawings

METHODS FOR CONTROLLING CROSS-HYBRIDIZATION IN ANALYSIS OF NUCLEIC ACID SEQUENCES

BACKGROUND OF THE INVENTION

1. Field of the Invention

This invention relates to methods and reagents for analyzing nucleotide sequences of nucleic acids and, more particularly, to methods for analyzing nucleotide sequences wherein cross-hybridization reactions are controlled.

Determining the nucleotide sequences and expression levels of nucleic acids (DNA and RNA) is critical to understanding the function and control of genes and their relationship, for example, to disease discovery and disease management. Analysis of genetic information plays a crucial role in biological experimentation. This has become especially true with regard to studies directed at understanding the fundamental genetic and environmental factors associated with disease and the effects of potential therapeutic agents on the cell. Such a determination permits the early detection of infectious organisms such as bacteria, viruses, etc.; genetic diseases such as sickle cell anemia; and various cancers. This paradigm shift has lead to an increasing need within the life science industries for more sensitive, more accurate and higher-throughput technologies for performing analysis on genetic material obtained from a variety of biological sources.

Unique or misexpressed nucleotide sequences in a polynucleotide can be detected by hybridization with a nucleotide multimer, or oligonucleotide, probe. Hybridization is based on complementary base pairing. When complementary single stranded nucleic acids are incubated together, the complementary base sequences pair to form double stranded hybrid molecules. These techniques rely upon the inherent ability of nucleic acids to form duplexes via hydrogen bonding according to Watson-Crick base-pairing rules. The ability of single stranded deoxyribonucleic acid (ssDNA) or ribonucleic acid (RNA) to form a hydrogen bonded structure with a complementary nucleic acid sequence has been employed as an analytical tool in molecular biology research. The oligonucleotide probe employed in the detection is selected with a nucleotide sequence complementary, usually exactly complementary, to the nucleotide sequence in the target nucleic acid. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present.

One method for detecting specific nucleic acid sequences generally involves immobilization of nucleic acid on a solid support such as nitrocellulose paper, cellulose paper, diazotized paper, or a nylon membrane. After the target nucleic acid is fixed on the support, the support is contacted with a suitably labeled nucleic acid for about two to forty-eight hours. After the above time period, the solid support is washed several times at a controlled temperature to remove unhybridized probe. The support is then dried and the hybridized material is detected by autoradiography or by spectrometric methods.

Another method for detecting specific nucleic acid sequences employs hybridization to surface-bound arrays of sample nucleic acid sequences or oligonucleotide probes. Such techniques are useful for analyzing the nucleotide sequence of target nucleic acids. In theory, and to some extent in practice, hybridization to surface-bound arrays can provide a relatively large amount of information in a single experiment. For example, array technology has identified single nucleotide polymorphisms within relatively long (1,000 residues or bases) sequences (Kozal, M., et al., Nature Med. 7:753–759, July 1996). In addition, array technology is useful for some types of gene expression analysis, relying upon a comparative analysis of complex mixtures of mRNA target sequences (Lockart, D., et al., (1996) Nat. Biotech. 14, 1675–1680).

In many assays there may be one or more non-target nucleic acids present that have a nucleotide sequence closely related to that of the target sequence differing by only a few, e.g., one to five nucleotides. In such cases the non-target polynucleotide may then interfere with the assay by hybridizing with at least some of the target probe to produce false qualitative or quantitative results. This problem is particularly acute where the probe sequence is selected to permit assaying of various genes within a multigene family, each member of which contains a sequence closely related to the target nucleotide sequence. In analysis by array technology there is the concern that cross-hybridization may occur, which would result in false positive signals.

Approaches have been suggested for alleviating some of the above concerns. One technique involves placing on an array intentionally mismatched control probes as well as the actual probe of interest. A mismatched probe has one or more base substitutions. By observing the signal for the original probe versus the mismatched probes one can gauge specificity and perhaps even correct for cross-hybridization by subtracting some fraction of the mismatch probe signal from the signal generated by the probe of interest. In a particular approach probes are generated by constructing all possible one base substitutions at a specific position near the center of the probe and synthesizing them next to the probe of interest. However, this mismatch strategy is relatively arbitrary and multiplies by 5 the number of array locations required to evaluate the performance of a single probe. In some arrays, the percentage of array locations devoted to mismatch probes is decreased by choosing a single base substitution. However, this choice is even more arbitrary than synthesizing all possibilities at a single position.

2. Description of the Related Art

An assay for polynucleotides employing oligonucleotides to eliminate undesirable cross-reactions is discussed in U.S. Pat. No. 5,434,047 (Arnold).

Arrays of nucleic acid probes on biological chips are disclosed in U.S. Pat. No. 5,837,832 (Chee, et al.).

Sapolsky, et al., discusses polymorphism detection in U.S. Pat. No. 5,858,659.

Genome-wide expression monitoring in Saccharomyces cerevisiae is described by Wodicka, et al., in Nature Biotechnology (1997) 15:1359–1367.

Mitsuhashi, et al., in U.S. Pat. No. 5,556,749 discuss a computerized method for designing optimal DNA probes and an oligonucleotide probe design station.

SUMMARY OF THE INVENTION

One embodiment of the present invention is a method for selecting a set comprising a set of target-specific oligonucleotide probes for use in analyzing a target nucleic acid sequence. A cross-hybridization oligonucleotide probe is identified based on a candidate target-specific oligonucleotide probe for the target nucleic acid sequence. The cross-hybridization oligonucleotide probe measures the extent of occurrence of a hybridization event having a predetermined probability. Cross-hybridization results are determined employing the cross-hybridization oligonucleotide probe and the target-specific oligonucleotide probe. The cross-hybridization results determine whether or not the target-specific oligonucleotide probe is selected for the set of target-specific oligonucleotide probes.

Another embodiment of the present invention is a method for analyzing a target nucleic acid sequence. A set of target-specific oligonucleotide probes is selected for each target nucleic acid sequence. A cross-hybridization oligonucleotide probe is identified based on a candidate target-specific oligonucleotide probe for each target nucleic acid sequence. The cross-hybridization oligonucleotide probe measures the extent of occurrence of a hybridization event having a predetermined probability. Cross-hybridization results are determined employing the cross-hybridization oligonucleotide probe and the target-specific oligonucleotide probe, which is included or excluded in the set based on the results. In the method of analysis, the set of target-specific oligonucleotide probes is contacted with a sample suspected of containing a target nucleic acid sequence. The extent of hybridization of the target-specific oligonucleotide probe to the target nucleic acid sequence is determined. Depending on the specificity of the target-specific oligonucleotide probe one or more cross-hybridization oligonucleotide probes, identified using the above method, may be employed in the analysis. The cross-hybridization results may be used to correct for hybridization events that are not due to the presence of the target nucleic acid sequence.

The selection of the cross-hybridization oligonucleotide probes may be carried out in a number of ways. In one approach selection is carried out by a process comprising determining homologous sequences in actual genes that meet predetermined criteria with respect to the oligonucleotide probe specific for the target nucleic acid sequence. In another approach selection of a minimum number of cross-hybridization probes is conducted by a process comprising incorporating a selected combination of possible nucleotide substitutions at one or more positions in a single cross-hybridization oligonucleotide probe. In another approach the selecting is carried out by a process comprising deleting nucleotides at one or more positions in a single cross-hybridization oligonucleotide probe. In yet another approach the selection is realized by a process comprising inserting nucleotides at one or more positions in a single cross-hybridization oligonucleotide probe.

Another embodiment of the present invention is a kit for analyzing a target nucleic acid sequence. The kit comprises in packaged combination (a) an oligonucleotide probe specific for the target nucleic acid sequence and (b) a cross-hybridization oligonucleotide probe, which is based on the target nucleic acid sequence. The cross-hybridization oligonucleotide probe measures the extent of the occurrence of a cross-hybridization event of a predetermined probability between an interfering nucleic acid sequence and the oligonucleotide probe specific for the target nucleic acid sequence.

Another embodiment of the present invention is a composition comprising a mixture of cross-hybridization oligonucleotide probes. A cross-hybridization result obtained with the mixture measures the extent of the occurrence of a cross-hybridization event of a predetermined probability between an interfering nucleic acid sequence and an oligonucleotide probe specific for a target nucleic acid sequence.

Another embodiment of the present invention is an addressable array comprising a support having a surface, a spot on the surface having bound thereto an oligonucleotide probe specific for a target nucleic acid sequence and at least one spot on the surface having bound thereto a cross-hybridization oligonucleotide probe wherein the cross-hybridization oligonucleotide probe measures the extent of the occurrence of a cross-hybridization event of a predetermined probability between an interfering nucleic acid sequence and the oligonucleotide probe specific for a target nucleic acid sequence. The probes are employed in an effective amount, namely, an amount that will yield the desired result such as detection of the target nucleic acid sequence.

Another embodiment of the present invention is a computer-based method for selecting a set of target-specific oligonucleotide probes for use in analyzing a target nucleic acid sequence. Under computer control a cross-hybridization oligonucleotide probe is identified based on the target nucleic acid sequence. The cross-hybridization oligonucleotide probe measures the extent of the occurrence of a cross-hybridization event having a predetermined probability. Under computer control cross-hybridization results are determined employing the cross-hybridization oligonucleotide probe and target-specific oligonucleotide probe. A selection or rejection of the target-specific oligonucleotide probe for the set based on the cross-hybridization results is carried out under computer control.

Another embodiment of the present invention is a computer system for selecting a set of target-specific oligonucleotide probes for use in analyzing a target nucleic acid sequence. Input means is provided for introducing one or more target nucleotide sequences into the computer system. Also included is means for determining cross-hybridization oligonucleotide probes based on the target nucleic acid sequences wherein the cross-hybridization oligonucleotide probes measure the extent of the occurrence of cross-hybridization events each having a predetermined probability. Memory means is included for determining cross-hybridization results employing the cross-hybridization oligonucleotide probes and target-specific oligonucleotide probes. The computer system further comprises means for storing the cross-hybridization results, means for controlling the computer system to select or reject the target-specific oligonucleotide probes for the set based on the cross-hybridization results, means for storing selection results, and means for outputting data relating to the selection results.

Another embodiment of the present invention is a computer program product comprising a computer readable storage medium having a computer program stored thereon which, when loaded into a computer, selects a set of target-specific oligonucleotide probes for use in analyzing a target nucleic acid sequence. The computer program performs steps comprising (a) identifying under computer control a cross-hybridization oligonucleotide probe based on the target nucleic acid sequence wherein the cross-hybridization oligonucleotide probe measures the extent of the occurrence of a cross-hybridization event having a predetermined probability, (b) determining under computer control cross-hybridization results employing the cross-hybridization oligonucleotide probe and target-specific oligonucleotide probe and (c) selecting or rejecting under computer control the target-specific oligonucleotide probe for the set based on the cross-hybridization results.

Another embodiment of the present invention is a method of designing oligonucleotide probes for distinguishing related sequences. First oligonucleotide probes that are sensitive to a first related sequence are identified. Second oligonucleotide probes to a second related sequence are also identified. The second oligonucleotide probes are homologous probes in the second related sequence that correspond to the first oligonucleotide probes in the first related sequence. The second oligonucleotide probes are scored based on measuring the likelihood of the second oligonucleotide probes to cross-hybridize to the second related sequence. A defined range of scores is indicative of oligonucleotide probes having a predetermined likelihood to hybridize to the first related sequence. The second oligonucleotide probes are selected on the basis of their scores determined above and are evaluated experimentally for their performance.

Another embodiment of the present invention is a method for detecting differences between an individual sequence and a known reference sequence. A labeled individual sequence, a surface bound reference oligonucleotide probe based on the known reference sequence and a set of surface bound deletion oligonucleotide probes are combined under hybridization conditions. The set of deletion oligonucleotide probes is prepared by a process comprising deleting nucleotides at one or more positions in a set of oligonucleotide probes corresponding to the reference oligonucleotide. Hybridization ratios are determined for the set of deletion oligonucleotide probes with respect to the reference oligonucleotide probe. The hybridization ratios are related to the presence or absence of differences between the individual sequence and the reference sequence.

DETAILED DESCRIPTION OF THE INVENTION

Terminology

The term "polynucleotide" or "nucleic acid" refers to a compound or composition that is a polymeric nucleotide or nucleic acid polymer. The polynucleotide may be a natural compound or a synthetic compound. The polynucleotide can have from about 2 to 5,000,000 or more nucleotides. The larger polynucleotides are generally found in the natural state. In an isolated state the polynucleotide can have about 10 to 50,000 or more nucleotides, usually about 100 to 20,000 nucleotides. It is thus obvious that isolation of a polynucleotide from the natural state often results in fragmentation. It may be useful to fragment longer target nucleic acid sequences, particularly RNA, prior to hybridization to reduce competing intramolecular structures.

The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

The nucleic acids may be generated by in vitro replication and/or amplification methods such as the Polymerase Chain Reaction (PCR), asymmetric PCR, the Ligase Chain Reaction (LCR), transcriptional amplification by an RNA polymerase, and so forth. The nucleic acids may be either single-stranded or double-stranded. Single-stranded nucleic acids are preferred because they lack complementary strands that compete for the oligonucleotide probes during the hybridization step of the method of the invention. A nucleic acid may be treated to render it denatured or single stranded by treatments that are well known in the art and include, for instance, heat or alkali treatment, or enzymatic digestion of one strand.

The phrase "target nucleic acid sequence" refers to a sequence of nucleotides to be identified, detected or otherwise analyzed, usually existing within a portion or all of a polynucleotide. In the present invention the identity of the target nucleotide sequence may be known to an extent sufficient to allow preparation of various sequences hybridizable with the target nucleotide sequence and of oligonucleotides, such as probes and primers, and other molecules necessary for conducting methods in accordance with the present invention, related methods and so forth.

The target sequence usually contains from about 10 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of identification, detection, amplification, and/or other analysis of the target nucleotide sequence, where appropriate.

It is to be noted that the usage of the terms "probe" and "target" in the literature may vary. For example, when describing non-homogeneous diagnostic assays, the term "probe" may be used to refer to an immobilized or surface-bound species, and the term target may be used to refer to a species in solution (the "target" of the assay). Such usage of the terms is the opposite of the usage sometimes seen in the molecular biology literature. The present application uses the diagnostic assay definitions of the terms "probe" and "target" as discussed herein.

The term "oligonucleotide" refers to a polynucleotide, usually single stranded, either a synthetic polynucleotide or a naturally occurring polynucleotide. The length of an oligonucleotide is generally governed by the particular role thereof, such as, for example, probe, primer and the like. Various techniques can be employed for preparing an oligonucleotide. Such oligonucleotides can be obtained by biological synthesis or by chemical synthesis. For short oligonucleotides (up to about 100 nucleotides), chemical synthesis will frequently be more economical as compared to biological synthesis. In addition to economy, chemical synthesis provides a convenient way of incorporating low molecular weight compounds and/or modified bases during specific synthesis steps. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. Methods of oligonucleotide synthesis include phosphotriester and phosphodiester methods (Narang, ET al. (1979) Meth. Enzymol 68:90) and synthesis on a support (Beaucage, et al. (1981) Tetrahedron Letters 22:1859–1862) as well as phosphoramidite techniques (Caruthers, M. H., et al., "Methods in Enzymology," Vol. 154, pp. 287–314 (1988)) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., Proc. Nat. Acad. Sci. USA (1994) 91:5022–5026.

Oligonucleotides may be employed, for example, as oligonucleotide probes or primers. The term "oligonucleotide probe" refers to an oligonucleotide employed to bind to a portion of a polynucleotide such as another oligonucleotide or a target nucleotide sequence. The design, including the length, and the preparation of the oligonucleotide 10 probes are generally dependent upon the sequence to which they bind. Usually, the oligonucleotide probes are at least about 2 nucleotides, preferably, about 5 to about 100 nucleotides, more preferably, about 10 to about 50 nucleotides, and usually, about 15 to about 30 nucleotides, in length. The term "oligonucleotide primer(s)" refers to an oligonucleotide that is usually employed in a chain extension on a polynucleotide template such as in, for example, an amplification of a nucleic acid.

The phrase "nucleoside triphosphates" refers to nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized and polymerized in a similar manner to the underivatized nucleoside triphosphates.

The term "nucleotide" or "nucleotide base" or "base" refers to a base-sugar-phosphate combination that is the monomeric unit of nucleic acid polymers, i.e., DNA and RNA. The term as used herein includes modified nucleotides. In general, the term refers to any compound containing a cyclic furanoside-type sugar (β-D-ribose in RNA and β-D-2'-deoxyribose in DNA), which is phosphorylated at the 5' position and has either a purine or pyrimidine-type base attached at the C-1' sugar position via a β-glycosol C1'-N linkage. The nucleotide may be natural or synthetic.

The term "DNA" refers to deoxyribonucleic acid.

The term "RNA" refers to ribonucleic acid.

The term "nucleoside" refers to a base-sugar combination or a nucleotide lacking a phosphate moiety.

The terms "hybridization (hybridizing)" and "binding" in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like.

The term "complementary," "complement," or "complementary nucleic acid sequence" refers to the nucleic acid strand that is related to the base sequence in another nucleic acid strand by the Watson-Crick base-pairing rules. In general, two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G/U or U/G basepairs.

The term "hybrid" refers to a double-stranded nucleic acid molecule formed by hydrogen bonding between complementary nucleotides. The term "hybridize" refers to the process by which single strands of nucleic acid sequences form double-helical segments through hydrogen bonding between complementary nucleotides.

The term "support" or "surface" refers to a porous or non-porous water insoluble material. The support can have any one of a number of shapes, such as strip, plate, disk, rod, particle, including bead, and the like. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; flat glass whose surface has been chemically activated to support binding or synthesis of polynucleotides, glass available as Bioglass, ceramics, metals, and the like. Natural or as synthetic assemblies such as liposomes, phospholipid vesicles, and cells can also be employed. Binding of oligonucleotides to a support or surface may be accomplished by well-known techniques, commonly available in the literature. See, for example, A. C. Pease, et al., Proc. Nat. Acad. Sci. USA, 91:5022–5026 (1994).

The term "related sequences" refers to sequences having a variation in nucleotides such as in a "mutation," for example, single nucleotide polymorphisms. In general, the variations occur from individual to individual. The mutation may be a change in the sequence of nucleotides of normally conserved nucleic acid sequence resulting in the formation of a mutant as differentiated from the normal (unaltered) or wild-type sequence. Point mutations (i.e. mutations at a single base position) can be divided into two general classes, namely, base-pair substitutions and frameshift mutations. The latter entail the insertion or deletion of a nucleotide pair. Mutations that insert or delete multiple base pairs are also possible; these can leave the translation frame unshifted, permanently shifted, or shifted over a short stretch of sequence. A difference of a single nucleotide can be significant so to change the phenotype from normality to abnormality as in the case of, for example, sickle cell anemia.

Methods and Compositions of the Invention

In General

In a broad aspect the present invention concerns a method for selecting a set of oligonucleotide probes that are specific for a target nucleic acid sequence. The method may also be employed to select a set comprising a minimum number of cross-hybridization control oligonucleotide probes for use, if necessary, in analyzing a target nucleic acid sequence. The target-specific oligonucleotide probes may be employed in a method for analyzing a target nucleic acid sequence. Using the present invention one can select target-specific oligonucleotide probes that are sufficiently specific so that cross-hybridization of such probes with interfering sequences that may be present in the sample does not significantly affect the ability to detect the target sequence. In this circumstance the target-specific oligonucleotide probes may be employed in the method of analysis without using cross-hybridization probes. However, if one is not able to achieve the above, then, the present invention provides for identifying a minimum number of cross-hybridization oligonucleotide probes that may be used in conjunction with the target-specific oligonucleotide probes to reduce the impact of such cross-hybridization events to an acceptable level by providing means for measuring a correction factor that partially or completely cancels the signal generated by cross-hybridization events. It is further within the purview of the present invention to use the identified cross-hybridization probes to adjust the signal obtained so that the method of analysis will result in an accurate measurement of the amount of the target nucleic acid sequence.

In the present method a cross-hybridization oligonucleotide probe is identified based on a candidate target-specific oligonucleotide probe for the target nucleic acid sequence. The candidate target oligonucleotide probe may be selected based on information about the target nucleic acid sequence using one of a number of different methods as discussed below. The cross-hybridization oligonucleotide probe measures a signal that can be used to estimate the extent of the occurrence of a cross-hybridization event between the target-specific oligonucleotide probe and an interfering sequence having a predetermined probability.

The nature of the predetermined probability is related to the particular method used to select the cross-hybridization probes as discussed more fully hereinbelow. In general, the extent of the occurrence of a cross-hybridization event is one that is predicted to be highly probable or most probable. Cross-hybridization probes are identified based on a certain threshold level, which may be adjusted on a case by case basis to assure that a sufficient number of probes are included for consideration. Then, probes within this group are further identified based on a predetermined percentage of those in the threshold group such as, for example, those in the top 25%, the top 20%, the top 15%, the top 10%, the top 5%, or the top 1%. The particular percentage chosen is dependent on the strength of the association of the target nucleic acid sequence with the target-specific oligonucleotide probe, on the relative concentration of the target nucleic acid sequence and the interfering sequence, and the like. The percentages may be related to the particular scoring scheme used. For example, where the scoring scheme involves predicted melting temperatures (Tm), those oligonucleotide probes having a Tm that is within 10 degrees, or within 5 degrees, of that of a perfect match would be under consideration for potentially addressing a sequence that would result in substantial interference with detection of a target nucleic acid sequence. Where the scoring scheme involves predicted free energy of interaction, those oligonucleotide probes having a ΔG that is within 3 kcal/mole, or within 1.5 kcal/mole, of that of a perfect match would be under consideration for potentially addressing a sequence that would result in substantial interference with detection of a target nucleic acid sequence.

Setting the threshold involves two factors. The factor relates to how many positions on an array are available or, stated another way, how many probes can one afford to synthesize for the array. The second factor relates to experimental experience. Candidate cross-hybridization probes are subjected to experimental analysis to determine how well a particular scoring scheme is working to identify cross-hybridization probes to interfering sequences that are of most concern with respect to a particular target polynucleotide. Part of this latter factor relates to how many cross-hybridization oligonucleotide probes are necessary to address such interfering sequences.

A cross-hybridization event may be evaluated using any method that will allow such an evaluation. Examples of such methods, by way of illustration and not limitation, are discussed in detail below. Cross-hybridization levels are estimated employing the target-specific oligonucleotide probe and a related cross-hybridization oligonucleotide probe. Based on the cross-hybridization results, the target-specific oligonucleotide probe is included in, or excluded from, the set of target-specific oligonucleotide probes used to perform a particular assay. The above steps may be repeated to determine a set of target-specific oligonucleotide probes and a set of cross-hybridization oligonucleotide probes, both of the sets comprising one or a minimum number of such probes.

A primary focus of the present invention is to provide for more efficient design of target-specific oligonucleotide probes and/or cross-hybridization oligonucleotide probes and thereby to reduce to a minimum the number of such probes that are utilized in analyzing a target nucleic acid sequence. In one aspect the present approach is directed to the design of controls in nucleic acid hybridization assays. Once the controls are designed, the resulting selected cross-hybridization probes may be used in experiments with actual samples, which may be limited in amount. Accordingly, the amount of actual test sample employed in an analysis may be conserved.

In essence in the present invention, one seeks to generalize information about how specific and sensitive a potential cross-hybridization probe is and to choose a set of cross-hybridization probes based thereon wherein the set comprises a minimum number of such probes. The present invention addresses a potential situation that is of concern. In a complex sample, there may be one or more target sequences, i.e., interfering sequences, which form an imperfect match with a particular oligonucleotide probe, which then hybridizes with such sequence as well as to the target nucleic sequence if present. The point is, however, that binding to this oligonucleotide probe produces a signal whether or not the target nucleic acid sequence is present. This signal is interpreted as detection of the intended target, leading to a false-positive assay result.

In the present invention a set of cross-hybridization oligonucleotide probes is selected for each target nucleic acid sequence. The set of probes comprises a minimum number, which is less that a full set, of cross-hybridization oligonucleotide probes for each target nucleic acid sequence. The selection of this minimal set is performed by taking advantage of knowledge of other, related sequences present in the target sample, constructing cross-hybridization probes or probe mixtures that effectively model multiple mismatched target possibilities, or combining these two approaches. The cross-hybridization results obtained with the set either target cross-hybridization events having a predetermined probability, e.g., the most likely or most probable cross-hybridization events, or are substantially the same as an average of results obtained with a larger number, such as a full set, of cross-hybridization oligonucleotide probes. In one aspect of the present method, the set of target-specific and matched cross-hybridization oligonucleotide probes is contacted with a target nucleic acid sequence. The differential hybridization of the target-specific and matched cross-hybridization oligonucleotide probes to the target sample is determined, and the specificity of hybridization of the target-specific probe to its intended target sequence is estimated employing the cross-hybridization results.

Cross-hybridization oligonucleotide probes are oligonucleotide probes that may be used in conjunction with the target-specific oligonucleotide probes. The cross-hybridization (or mismatch) oligonucleotide probes are directed to sequences (interfering sequences or inappropriate sequences) that may be present that are capable of hybridizing with the target-specific oligonucleotide probe. If the target-specific probe is 25 bases long, the number of potential cross-hybridizing sequences is $\sim 4^{25}$ or $1.13 \times 10^{15}$. Obviously, a real experiment can sample only a tiny fraction of these possibilities; even experiments that employ a seeming abundance of cross-hybridization probes are, in reality, measuring results from a sparse collection of the possible cross-hybridization events.

As mentioned above, a minimum number of cross-hybridization oligonucleotide probes are utilized in the present invention for each target nucleic acid sequence. The minimum number is less than a larger number, such as a full set, of cross-hybridization oligonucleotide probes for each target nucleic acid sequence. The minimum number of cross-hybridization oligonucleotide probes is dependent on the nature of the target nucleic acid sequence and the nature and number of sequences that may interfere with the detection of the target nucleic acid sequence as explained more fully below. Usually, the minimum number of cross-hybridization oligonucleotide probes per gene is no more than about 10, more usually, no more than about 5, and may be as few as one. This is to be contrasted with a larger number of cross-hybridization oligonucleotide probes that are used in the prior art. The number of such probes per gene in prior art methods of gene expression-level measurement is usually at least about 20 and may be as high as 100 or more.

The focus of the present invention is to use as few a number of cross-hybridization oligonucleotide probes as necessary to achieve the level of specificity and sensitivity achieved with a larger number of such probes. Desirably, a single cross-hybridization oligonucleotide probe is determined and used. On the other hand, a set of cross-hybridization oligonucleotide probes may be determined wherein the cross-hybridization result obtained with the set measures the extent of occurrence of hybridization events that have a predetermined probability based on certain information about the target nucleic acid sequence and the target-specific oligonucleotide probe. Accordingly, the cross-hybridization results obtained with the minimum number of cross-hybridization probes indicate that cross-hybridization is or is not a problem as well as or better than the results obtained with a larger number of such probes. The results are obtained from an analysis, or hybridization study, of a sample suspected of containing a target nucleic acid sequence using a target-specific oligonucleotide probe and one or more cross-hybridization oligonucleotide probes. The results are usually determined by measuring the signal produced in the analysis after hybridization studies have been conducted. Specificity ratios (i.e. the ratio of net signal from the target-specific oligonucleotide probe to the average of the signals from the matched cross-hybridization probes) greater than 2 are suggestive of a target-specific oligonucleotide probe of requisite specificity. Specificity ratios greater than 5 are generally interpreted as indicators of a target-specific oligonucleotide probe having good specificity.

The process for identifying and selecting the minimum number of cross-hybridization oligonucleotide probes may be carried out using different approaches in accordance with the present invention. Examples of such approaches, by way of illustration and not limitation, include mismatch probe design by homology, mismatch probes that incorporate base combinations, mismatch probes that delete bases, mismatch probes that insert bases, and the like, and combinations thereof.

Mismatch Probe Design by Homology

In one approach homology algorithms can be used to interrogate known gene databases for naturally occurring sequences that are closest to the original probe sequence. Such homology algorithms are known in the art or can be developed by those skilled in the art based on the disclosure contained herein. Known homology algorithms or search engines that may be employed in the present invention include BLAST (from the National Center for Biotechnology Information, NCBI; see S. F. Altschul, W. Gish, W. Miller, E. W. Myers, D. J. Lipman, *J Mol Biol* 215, 403–10 (1990)), thermodynamically-scored homology evaluation (see Mitsuhashi, et al., U.S. Pat. No. 5,556,749) and so forth.

A particular homology search or design may be, for example, one that returns the sequence in some specified database that contains the lowest number of mismatches against the oligonucleotide probe being analyzed. Such a search can return a list of possible mismatch probes that also match some specified criteria such as a specific number of mismatches and/or distribution of mismatches within the mismatched sequence. Priority may also be given to mismatch probes that are contained within reasonably homologous strains of the same or similar genomes. The search may focus on mismatches most likely to produce cross-hybridization. In this way mismatch probes are not simply arbitrary symbolic substitutions. The oligonucleotide probes selected represent sequences that have more than random chance of occurring in the sample. In another aspect the search can focus on thermodynamics. Accordingly, the search can comprise homologous sequences having a predicted free energy substantially the same as a predetermined predicted free energy of the hybridizing of the target-specific oligonucleotide probe with the target nucleic acid sequence.

In the mismatch probe design by homology, an array designer can target base substitutions that are most likely to actually cause problems. As mentioned above, homology search engines can be employed to look for homologous sequences in actual genes where the homologous sequences have a predetermined number of mismatches between the target-specific probe and the experimental probe. The advantage of using homology searches to generate mismatch probes is that the experimenter can potentially search against sequenced genomes and look for mismatch sequences that might actually appear in the sample. The resulting measurements, therefore, have significantly more meaning than a randomly chosen mismatch, which might not occur at all in nature.

Several scoring schemes can be used to evaluate the results of homology searches. Some commonly used schemes are as follows:

(a) Symbolic Match Score: In this scheme, the score is simply the number of identical bases encountered in a position-by-position comparison between a sequence of interest and a putative homologous sequence.

(b) Ungapped BLAST Score: This is the score calculated by the earliest forms of the Basic Local Alignment Search Tool (BLAST) algorithm. BLAST scores take into account both the number of symbolic matches observed and the probabilities of the observed types of matches, given real nucleotide frequencies and the nucleotide composition of the particular sequence of interest. Ungapped BLAST scoring schemes are discussed further by Altschul et al. (Altschul, S. F., Gish, W., Miller, W., Myers, E. W., and Lipman, D. J. (1990). "Basic local alignment search tool." *J Mol Biol*, 215(3), 403–410). A general tutorial can also be found at http://www.ncbi.nlm.nih.gov/BLAST/tutorial/Altschul-1.html (c) Gapped BLAST Score: This is the score calculated by more recent forms of the BLAST algorithm. Gapped BLAST scores include some effects of the distribution of sequence mismatches, as well as the effects of all of the factors that enter into ungapped BLAST scores. A general tutorial on gapped BLAST scores can be found at http://www.ncbi.nlm.nih.gov/BLAST/tutorial/Altschul-1.html (d) Thermodynamic Scores: All of these scores are based on the estimation of the enthalpy ($\Delta H$) and entropy ($\Delta S$) of interaction of the surface-bound probe polynucleotide and solution target polynucleotide, using an accepted model. Parameters and methods for calculating duplex enthalpies and entropies of perfectly matched, complementary polynucleotides are described by SantaLucia, et al. (SantaLucia, J., Allawi, H. T., and Seneviratne, P. A. (1996). "Improved nearest-neighbor parameters for predicting DNA duplex stability." *Biochemistry*, 35(11), 3555–3562). Parameters and methods for including the effects of mismatched bases are described in Allawi, H. T., and SantaLucia, J., Jr. (1997). "Thermodynamics and NMR of internal G.T mismatches in DNA." *Biochemistry*, 36(34), 10581–10594. Allawi, H. T., and SantaLucia, J., Jr. (1998). "Nearest neighbor thermodynamic parameters for internal G.A mismatches in DNA." *Biochemistry*, 37(8), 2170–2179. Allawi, H. T., and SantaLucia, J., Jr. (1998). "Nearest-neighbor thermodynamics of internal A.C mismatches in DNA: sequence dependence and pH effects." *Biochemistry*, 37(26), 9435–9444. Allawi, H. T., and SantaLucia, J., Jr. (1998). "Thermodynamics of internal C.T mismatches in DNA." *Nucleic Acids Res.*, 26(11), 2694–2701. Peyret, N., Seneviratne, P. A., Allawi, H. T., and SantaLucia, J., Jr. (1999). "Nearest-neighbor thermodynamics and NMR of DNA sequences with internal A.A, C.C, G.G, and T.T mismatches." *Biochemistry*, 38(12), 3468–3477. Enthalpies and entropies are commonly used to calculate two other quantities: duplex free energy ($\Delta G$) and duplex melting temperature ($T_m$):

$$\Delta G = \Delta H - T\Delta S,$$

where T is the temperature in ° K, and $$T_m = \frac{\Delta H}{\Delta S + R \ln [\text{target}]} - 273.15°,$$

where R is the gas constant (1.987 cal/(mole-° K)), [target] is the target concentration (M) and $T_m$ is measured in ° C. The effect of [target] is small, and therefore an estimate between $10^{-10}$ and $10^{-9}$ M is usually used. Finally, the free energies of interaction between the specific probe and all the homologues found by some search algorithm (e.g. BLAST) can be used along with estimates of target frequency to calculate a partition function Z. If $f_j$ is the frequency of the $j^{th}$ homologous target, $\Delta G_{ij}$ is the free energy of interaction between the $i^{th}$ probe and $j^{th}$ target, and interaction with the specific target occurs when j=i, then $$Z \equiv \sum_j f_j e^{\frac{-\Delta G_{ij}}{RT}}.$$

The partition function can then be used to calculate various scores, such as $$S_{ij} \equiv \frac{f_j e^{\frac{-\Delta G_{ij}}{RT}}}{Z}.$$

Such scores can also be used to estimate the importance of various potential cross-hybridization events.

(e) Score Thresholds: For each type of score, there exists some threshold score or score rank above which a potential cross-hybridization event is of concern. For symbolic match and BLAST scores, score rank is used: the top 5 scores should be investigated if possible, and the top 1 or 2 scores should always be investigated. For $\Delta G$, if $\Delta G_{ii} - G_{ij} < 3$ kcal/mole, then the interaction between the $i^{th}$ probe and the $j^{th}$ target should be investigated if possible; if $\Delta G_{ii} - G_{ij} < 1.5$ kcal/mole, then the interaction should definitely be investigated. For $T_m$, differences between target-specific and cross-hybridization predicted duplex melting temperatures that are less than 10° C. should be investigated if possible. Differences of less than 5° C. should always be investigated. Finally, for scores based on partition functions, thresholds may be set on the basis of validation studies.

In a particular example in accordance with the present invention, by way of illustration and not limitation, consider the 25-mer probe that begins at position 1230 of the yeast gene YER019W, and its nearest match in the yeast genome, the sequence beginning at position 226 of yeast gene YML018C:

| YER019W-1230 | GGTCGTGACAACGTTTACTGCAAAC | (SEQ ID NO: 1) |
|---|---|---|
| | ‖ ‖‖‖  ‖‖‖‖‖ ‖‖ ‖‖ ‖‖‖ | |
| YML018C-0226 | GGCCGTGCAAACGTTCACCGCGAAC | (SEQ ID NO: 2) |

Probe YML018C is found by a homology search algorithm, which returns the sequence that contains the lowest number of mismatches against the probe being analyzed. The target of this probe is the most likely target to cross-hybridize to the original probe, based on the symbolic matching method of scoring homology. Having identified this probe, its performance is then evaluated as discussed herein.

Suppose that the only target sequences that hybridize to the original probe (henceforth designated as a) are its intended target A and the target B of the nearest homologous probe, b. Then, the signal (discussed more fully hereinbelow) $S_a$ measured by probe a is the sum of two components:

$$S_a = S(aA) + S(aB), \quad \text{(Eqn. 1)}$$

where S(aA) is the signal due to binding of target A by probe a and S(aB) is the signal due to binding of target B by probe a. Similarly, $$S_b = S(bA) + S(bB), \quad \text{(Eqn. 2)}$$

where S(bA) is the signal due to binding of target A by probe b and S(bB) is the signal due to binding of target B by probe b. Now, suppose that the response (i.e. target binding by probes) is linear (i.e. proportional to target concentration). Then, $$S(aA) = K_{aA}[A]; \quad \text{(Eqn. 3)}$$

$$S(bB) = K_{bB}[B], \quad \text{(Eqn. 4)}$$

where [A] and [B] are the concentrations of targets A and B, and $K_{aA}$, $K_{bB}$ are the constants of proportionality.

Suppose further that the cross hybridization signal is also proportional to target concentration:

$$S(aB) = K_{aB}[B]; \quad \text{(Eqn. 5)}$$

$$S(bA) = K_{bA}[A], \quad \text{(Eqn. 6)}$$

where $K_{aB}$ and $K_{bA}$ are again constants of proportionality. Finally, assume that the proportionality constant for cross-hybridization of a probe to a homologous target is some fraction of the proportionality constant for hybridization of that probe to its intended target. Define constants α, β such that $$K_{aB} = \alpha K_{aA}; \quad \text{(Eqn. 7)}$$

$$K_{bA} = \beta K_{bB}; \quad \text{(Eqn. 8)}$$

Then, $$S(aB) = \alpha K_{aA}[B]; \quad \text{(Eqn. 9)}$$

$$S(bA) = \beta K_{bB}[A]; \quad \text{(Eqn. 10)}$$

If the probes behave reasonably (i.e., perfectly matched probes hybridize to their intended target sequences more strongly than imperfectly matched probes), then $$0 \leq \alpha \leq 1 \text{ and } 0 \leq \beta \leq 1. \quad \text{(Eqn. 11)}$$

The definitions of the measured signals can now be rewritten as $$S_a = K_{aA}([A] + \alpha[B]), \quad \text{(Eqn. 12)}$$

$$S_b = K_{bB}([B] + \beta[A]), \quad \text{(Eqn. 13)}$$

Define $\gamma = [B]/[A]$. Then, the ratio of the signal from control probe b to the signal from the probe of interest a is given by $$\frac{S_b}{S_a} = \left(\frac{\gamma + \beta}{1 + \gamma\alpha}\right)\frac{K_{bB}}{K_{aA}}. \quad \text{(Eqn. 14)}$$

Now, suppose that the value of the ratio $S_b/S_a$ is substantially less than 1. That implies that the ratio of proportionality constants $K_{bB}/K_{aA}$ is $\ll 1$ (i.e., target B is less accessible to probe b than target A is to probe a), or the ratio $(\gamma+\beta)/(1+\gamma\alpha)$ is $\ll 1$, or both. If target B is less accessible than target A in the region of homology (i.e., probed by a & b), then cross-hybridization is unlikely to occur, because the same secondary and tertiary structural factors that prevent target B from binding to probe b will prevent it from binding to probe a. Suppose alternatively that the ratio $(\gamma+\beta)/(1+\gamma\alpha)$ is $\ll 1$. There are 3 regimes of behavior (based on the value of γ) that are worth considering:

$$[A] \gg [B] | \gamma \to 0 (\gamma+\beta)/(1+\gamma\alpha) \to \beta$$

$$[A] \ll [B] | \gamma \to \infty (\gamma+\beta)/(1+\gamma\alpha) \to 1/\alpha$$

$$[A] = [B] | \gamma \to 1 (\gamma+\beta)/(1+\gamma\alpha) \to (1+\beta)/(1+\alpha)$$

Now, because α and β are always between 0 and 1, there is only one way that the quantity $(\gamma+\beta)/(1+\gamma\alpha)$ can be small: [A] $\gg$[B] and β$\ll$1. But if [A] $\gg$[B], the chances of significant cross-hybridization of target B to probe a are small. Therefore, the smaller the value of the ratio $S_b/S_a$, the better the chance that cross-hybridization of target B to probe a is not a problem.

Note that a value of $S_b/S_a \geq 1$ does not imply that cross-hybridization must be a problem; it only indicates that it might be, and further work may be done using the present methods to rule out the possibility. An important point is that mismatch probes designed by the above method yield data that is subject to rigorous, quantitative interpretation, and the data measured by such probes can be used to rule out the presence of certain varieties of cross-hybridization.

Mismatch Probes that Incorporate Base Combinations

In another approach in accordance with the present invention, mismatch probes can be constructed that incorporate a mixture of all three single base substitutions in one or more positions. This leads to, for example, an array feature that measures the average of the signals that would be produced by the 3 possible single base substitution probes employed in the prior art approach, the 9 possible probes produced by all possible substitutions at 2 bases, etc.

The profligate use of available probe positions by mismatch probe strategies that involve synthesis of all of the single-base substitution probe for a given nucleotide position is ameliorated in the present invention by incorporating all 3 substitution possibilities at a given position in a single probe position. If array synthesis is performed by either in situ phosphoramidite chemistry or conventional phosphoramidite chemistry followed by deposition and linkage of whole oligonucleotides to the surface, then such a combination probe can easily be synthesized by using a mixture of phosphoramidites to perform the synthetic step at the desired position.

The general case of substituting base combinations for a single base is most easily expressed using standard nucleotide "wobble codes," which means that letters are assigned to represent equimolar mixtures of bases at given sequence positions:

| Single Base Codes | Combinations of 2 Bases | Combinations of 3 Bases | Combinations of 4 Bases |
|---|---|---|---|
| A | A + C = M | A + C + G = V | A + T + G + C = N |
| T | A + G = R | A + C + T = H | |
| G | A + T = W | A + G + T = D | |

-continued

| Single Base Codes | Combinations of 2 Bases | Combinations of 3 Bases | Combinations of 4 Bases |
|---|---|---|---|
| C | C + G = S<br>C + T = Y<br>G + T = K | C + G + T = B | |

Then, for example, the 3-way mismatch probe at position 12 for the exact-match probe

GTCCATCCACCTCCGTTAAGCGTGC (SEQ ID NO:3) (YER019W-25-0618)

is written as

GTCCATCCACCVCCGTTAAGCGTGC (SEQ ID NO:4), which is shorthand for an equimolar combination of the following 3 probes in one probe location:

GTCCATCCACCACCGTTAAGCGTGC (SEQ ID NO:5)

GTCCATCCACCGCCGTTAAGCGTGC (SEQ ID NO:6)

GTCCATCCACCCCCGTTAAGCGTGC (SEQ ID NO:7)

The signal measured by this probe is the average of the signals that would be measured by the 3 individual probes that have been combined into one probe feature. If this signal is greater than or equal to the signal from the probe of interest, it indicates a significant probability that the signal from the probe of interest was partially or totally due to cross-hybridization.

This approach can be generalized to substitutions at more than one position. For instance, the substitution probe for positions 12 and 13 would be written as

GTCCATCCACCVDCGTTAAGCGTGC (SEQ ID NO:8), which is shorthand for an equimolar combination of the following 9 probes in one probe location:

GTCCATCCACCAACGTTAAGCGTGC (SEQ ID NO:9)

GTCCATCCACCATCGTTAAGCGTGC (SEQ ID NO:10)

GTCCATCCACCAGCGTTAAGCGTGC (SEQ ID NO:11)

GTCCATCCACCGACGTTAAGCGTGC (SEQ ID NO:12)

GTCCATCCACCGTCGTTAAGCGTGC (SEQ ID NO:13)

GTCCATCCACCGGCGTTAAGCGTGC (SEQ ID NO:14)

GTCCATCCACCCACGTTAAGCGTGC (SEQ ID NO:15)

GTCCATCCACCCTCGTTAAGCGTGC (SEQ ID NO:16)

GTCCATCCACCCGCGTTAAGCGTGC (SEQ ID NO:17)

The signal measured by this probe is the average of the signals that would be measured by the 9 individual probes that have been combined into one probe feature. Again, if this signal were greater than or equal to the signal from the probe of interest, it would indicate a significant probability that the signal from the probe of interest was partially or totally due to cross-hybridization.

Finally, it should be noted that this approach to constructing mismatch probes is particularly advantageous where an array is manufactured by printing phosphoramidites, since addition of the ability to write 3-way wobble bases to the writer simply involves adding four extra printing heads (one for each possible mixture of three bases). This is much less expensive than the addition of an entire extra masking step that would be required if the array were synthesized via photolithography.

Mismatch Probes that Delete Bases

In another approach in accordance with the present invention, one or more bases can be deleted from a specific position in the original probe. A deletion probe is sensitive to cross-hybridization by a "bridging" mechanism discussed herein. For example, consider the following cross-hybridization structure (wherein the sequence attached to the surface is SEQ ID NO:18 and the target is SEQ ID NO:19):

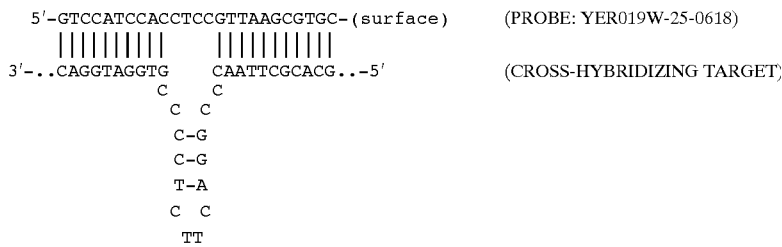

This sort of "bridging" structure forms with single-base substitution mismatch probes that changed bases 1, 12, 13 or 14 of the probe. It may also form with a probe that deleted one of these bases. Therefore, a deletion can be used to estimate the importance of this class of cross-hybridization. Accordingly, base substitutions, either alone or in combination, are not the only means by which one can estimate cross-hybridization.

Deletion probes have certain advantages over other mismatch probes. First, deletion probes are unambiguous for any given position in the probe, since there is only one way to delete a base. Second, the binding effects of a deletion are approximately equivalent to the effects of a single base substitution at the same position; therefore, the signal from a deletion probe can be interpreted by methods similar to those used to interpret mismatch control probe signals. Third, any apparatus that can synthesize polynucleotide arrays can synthesize this class of mismatch probe, without modification of the apparatus. Furthermore, this class of mismatch probes can easily be generalized to probes that contain more than one deletion.

Mismatch Probes that Insert Bases

In another approach in accordance with the present invention, one or more bases (or base combinations) can be inserted at specified positions; the resulting probe is particularly sensitive to "bridging" cross-hybridization. For example, the probe GTCCATCCACCTCCGTTAAGCGTGC (SEQ ID NO:20) (YER019W-25-0618)
could be paired with the insertion mismatch probe
GTCCATCCACCTNCCGTTAAGCGTGC (SEQ ID NO:21).

In the example above, the four-fold degenerate wobble code "N" indicates that the probe location actually contains an equimolar mixture of oligonucleotides that incorporate all four possible insertions at this location. It should be noted that insertion probes, like deletion probes, impose only a slightly greater energetic penalty than substitution mismatch probes for binding of the intended target of the parent probe. This class of mismatch probe is easily generalized to multiple insertions at one or more locations.

Combination of the Above Approaches

It is also with the purview of the present invention to combine one or more of the above approaches. For example, the approach involving design by homology discussed above can be combined with the one or more of the other approaches to produce mismatch probes that are more highly targeted towards the cross-hybridization events that are most likely to occur.

In a particular example, wobble-base substitutions were combined with probes designed by homology to a probe of interest. A homology search for target nucleic acid sequences whose coding strands are homologous to the nucleic acid probe YFL039C-25-0713 was performed using the WU-BLAST2 facility publically available via the Stanford Genomic Resources World Wide Web site http://genome-www.stanford.edu. The target of this probe is the complementary DNA or RNA derived via reverse-transcription of the mRNA produced by the yeast gene YFL039C (yeast β-actin gene). The target of the search was the set of all annotated yeast open reading frames (ORF's); since the yeast genome has been completely sequenced, this list is essentially complete. The comparison matrix was the program default (BLOSUM62), the cutoff score value was selected as 30 and the expectation threshold was selected as 1000. The search identified two homologous sequences that met the search criteria, did not contain gaps and ocurred on the coding strands of the corresponding ORFs:

```
CATCCAAGCCGTTTTGTCCTTGTAC   (SEQ ID NO:22) (YFL039C-25-0983)

TCCAAGCCGTTTTtTC          (SEQ ID NO:23) (YCL045C-16-0065)

ATCCAAGCCGTTTTcT           (SEQ ID NO:24) (YFR030W-16-1561)
``` where lower case (bold) denotes a changed base. In this example, the homology search yielded two possibilities for a changed base at position 16 of the original probe. In this case, the mismatch control probe of choice (or the "best" such probe) would be the probe

ATCCAAGCCGTTTTYTC (SEQ ID NO:25), where Y denotes a combination of T and C, and both the 5'-terminal A from YCL045C and the 3'-terminal C from YFR030W have been included. This simple example illustrates how the ability to include degenerate base combinations in mismatch control probes improves the ability of a single probe to control for multiple cross-hybridization possibilities.

The following discussion is provided by way of example and not limitation to further illustrate the use of the above method in nucleic acid analysis. Candidate target-specific oligonucleotide probes are chosen by approaches known in the art. For example, the candidate probes may be chosen by a method disclosed in U.S. patent application Ser. No. 09/021,701, filed Feb. 10, 1998. Briefly, this method involves predicting the potential of an oligonucleotide to hybridize to a target nucleotide sequence. A predetermined set of unique oligonucleotide sequences is identified. The unique oligonucleotide sequences are chosen to sample the entire length of a nucleotide sequence that is hybridizable with the target nucleotide sequence. At least one parameter that is predictive of the ability of each of the oligonucleotides specified by the set of sequences to hybridize to the target nucleotide sequence is determined and evaluated for each of the above oligonucleotide sequences. A subset of oligonucleotide sequences within the predetermined set of unique oligonucleotide sequences is identified based on the evaluation of the parameter. Finally, oligonucleotide sequences in the subset are identified that are clustered along one or more regions of the nucleotide sequence that is hybridizable to the target nucleotide sequence. This method for selecting probes is by way of illustration and not limitation. It is within the purview of the present invention to use any method for selection of appropriate target-specific oligonucleotide probes.

A hybridization experiment is then carried out using the candidate oligonucleotide probe that is specific for a particular target nucleic acid sequence. The intensity of signal is measured. Based on the level of signal, the candidate probe may be chosen for further experimentation or redesigned using an approach such as that described above. Cross-hybridization oligonucleotide probes are then selected.

The present method may be contrasted with an approach in accordance with the prior art. In the latter approach the entire set of single base mismatch probes at a central sequence position is prepared for all of target-specific probes complementary to a specified target region. This may be explained more fully as follows. Consider the target-specific oligonucleotide probe for the target nucleic acid sequence, selected as discussed above, is a 26-mer having the following sequence: CGAATCCGTTAGCAAACTGATGCATT (SEQ ID NO:26). A set of cross-hybridization oligonucleotide probes for the above based on one base mismatches at position 22 would be {CGAATCCGTTAGCAAACTGATc-CATT (SEQ ID NO:27), CGAATCCGTTAGCAAACT-GATaCATT (SEQ ID NO:28), and CGAATCCGTTAG-CAAACTGATtCATT (SEQ ID NO:29). Further probes could be synthesized at other positions, adding 3 probes per position examined.

However, in accordance with the present invention, a homology search, for example, is carried out that identifies a potential interfering sequence. The homology search is conducted to find the best match, i.e., the sequence with the best potential to interfere with the detection of the target sequence, in the genome or in highly expressed genes from an organism with which the target nucleic acid sequence is associated. As a result, such a sequence is identified that differs from the target nucleic acid sequence at bases 22–24. With this information a single cross-hybridization oligonucleotide probe is prepared having the following sequence: CGAATCCGTTAGCAAACTGATTACTT (SEQ ID NO:30).

An experiment is then conducted using the target-specific probe and the cross-hybridization probe. The sample containing the target nucleic acid sequence and the interfering sequence is placed on the surface of a support, to which the sequences bind. Then, the surface is contacted with the above oligonucleotide probes, which are labeled, and signal is measured. If the intensity of the signal from the target-specific probe is at a level that is considered reasonable, i.e., sufficiently detectable, and the intensity of signal from the cross-hybridization probe is negligible, then the interfering sequence is not much cause for concern. However, if the intensity of the signal from the cross-hybridization probe is equal to or greater than that from the target-specific probe, the interfering sequence may present a problem in an assay for the target nucleic acid sequence. In such a circumstance, additional evaluations or experiments in accordance with the present invention may be carried out to examine other cross-hybridization probes. In this manner the design of probes is perfected to achieve a set comprising a minimum number of cross-hybridization probes that provide the appropriate level of sensitivity and specificity. When this set of cross-hybridization oligonucleotide probes is employed with samples of unknown content, one has a higher degree of confidence that the results obtained are reliable.

The additional evaluations that may be carried out include searching for a different target-specific oligonucleotide probe that does not exhibit a potential for cross-hybridization and verifying that cross-hybridization is taking place by experimentally observing it. Picking a different probe is by far the easiest approach, if satisfactory alternative candidates are available. If the particulars of the experiment dictate that even a probe of mediocre specificity cannot be rejected, then the actual specificity of the probe can be measured by producing a synthetic version of the polynucleotide corresponding to the sequence to which the cross-hybridization probe hybridizes, using means well known to the art. This sequence or "cross-hybridization target" is then labeled in a manner easily distinguished from the normal experimental sample (e.g., a different, spectrally distinct fluorophore). The probe array is contacted with a mixture of the natural, complex sample and the synthetic sample, and the result of the contacting is determined. The result is usually determined by examining the array for the presence of hybrids. In this case signals from hybrids involving the target-specific probes and the cross-hybridization probes are observed. If the cross-hybridization target shows significant binding to the original target-specific probe, then the probe is not specific and should not be used without using the results of the cross-hybridization target experiment to correct for cross-hybridization. If the cross-hybridization target shows low binding to the original target-specific oligonucleotide probe and significant binding to the cross-hybridization probe, then the original cross-hybridization result is explained and can be dismissed. If neither probe shows significant binding of the cross-hybridization target, then the original result is unexplained, and there may be a problem with cross-hybridization to a third, unidentified target.

As mentioned above, one aspect of the present invention is a method for analyzing a target nucleic acid sequence. A set of target-specific oligonucleotide probes for the target nucleic acid sequence is selected. The method may involve one or more iterations of a process that comprises identifying a cross-hybridization oligonucleotide probe based on a candidate target-specific oligonucleotide probe for the target nucleic acid sequence, determining cross-hybridization results employing the cross-hybridization oligonucleotide probe and target-specific oligonucleotide probe together with a sample containing the target nucleic acid sequence and an interfering nucleic acid sequence, and including or excluding the target-specific oligonucleotide probe in the set based on the cross-hybridization results. The cross-hybridization oligonucleotide probe measures the extent of the occurrence of a hybridization event of a predetermined probability between the target-specific oligonucleotide probe and an interfering sequence, which may be present in the sample containing the target nucleic acid sequence. The process is repeated until a set of target-specific oligonucleotide probes is identified.

In the method of analysis the set of target-specific oligonucleotide probes is contacted with a sample suspected of containing a target nucleic acid sequence, and the extent of hybridization of the target-specific oligonucleotide probes to the target nucleic acid sequence is determined. During the analysis the sample may be contacted with one or more of the cross-hybridization oligonucleotide probes identified above. The use of such cross-hybridization probes would depend on whether sample-to-sample variation is such that cross-hybridization of the target-specific oligonucleotide probe and an interfering nucleic acid sequence may be a problem. In other words, although the present method may be used to select a set of target-specific oligonucleotide probes of high specificity, some samples to be tested may contain more of an interfering nucleic acid sequence than other samples. Alternatively, the best set of target-specific oligonucleotide probes obtained may still have some cross-hybridization with interfering nucleic acid sequences even though the amount of such interfering sequences does not vary significantly from one sample to the next. The method of the present invention provides an added advantage in that one may correct for cross-hybridization problems using the cross-hybridization probes identified by the present methods. By employing cross-hybridization oligonucleotide probes in accordance with the present invention, the relative amount of an interfering sequence can be measured and the overall signal obtained may be corrected to reflect only the amount of the target nucleic acid sequence.

The cross-hybridization oligonucleotide probe used in the above analysis may be a single probe obtained from a homology based method as described above. On the other hand the cross-hybridization probe may be part of a set of oligonucleotide probes wherein the cross-hybridization result obtained with the set is representative of a cross-hybridization event of a predetermined probability between the target-specific oligonucleotide probe and an interfering nucleic acid sequence.

The methods and reagents of the present invention are particularly useful in the area of oligonucleotide arrays. In the field of bioscience, arrays of oligonucleotide probes, fabricated or deposited on a surface, are used to identify DNA sequences in cell matter. The arrays generally involve a surface containing a mosaic of different oligonucleotides or sample nucleic acid sequences that are individually localized to discrete, known areas of the surface. In one approach, multiple identical arrays across a complete front surface of a single substrate are used. However, the arrays produced on a given substrate need not be identical and some or all could be different. Each array may contain multiple spots or features and each array may be separated by spaces. A typical array may contain from 100 to 100,000 features. All of the features may be different, or some or all may be the same. Each feature may carry a predetermined polynucleotide having a particular sequence or a predetermined mixture of polynucleotides. While arrays may be separated from one another by spaces, and the features may be separated from one another by spaces, such spaces in either instance are not essential.

Ordered arrays containing a large number of oligonucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

Various ways may be employed to produce an array of polynucleotides on supports or surfaces such as glass, metal, plastic and the like. Such methods are known in the art. One such method is discussed in U.S. Pat. No. 5,744,305 (Fodor, et al.) and involves solid phase chemistry, photolabile protecting groups and photolithography. Binary masking techniques are employed in one embodiment of the above. In another approach ink jet technology may be used to spot polynucleotides and other reagents on a surface as described, for example, in PCT application WO 89/10977. Other methods include those disclosed by Gamble, et al., WO97/44134; Gamble, et al., WO98/10858; Baldeschwieler, et al., WO95/25116; Brown, et al., U.S. Pat. No. 5,807,522; and the like.

In the above approaches to forming arrays, the chemistry involved may include monomers that are nucleoside triphosphates used to form the polynucleotides usually by phosphate coupling, either direct phosphate coupling or coupling using a phosphate precursor such as a phosphite coupling. Such coupling thus includes the use of amidite (phosphoramidite), phosphodiester, phosphotriester, H-phosphonate, phosphite halide, and the like coupling. One preferred coupling method is the phosphoramidite coupling, which is a phosphite coupling. In using this coupling method, after the phosphite coupling is complete, the resulting phosphite is oxidized to a phosphate. Oxidation can be effected with oxygen to give phosphates or with sulfur to give phosphorothioates. The phosphoramidites are dissolved in anhydrous acetonitrile to give a solution having a given ratio of amidite concentrations. The mixture of known chemically compatible monomers is reacted to a solid support, or further along, may be reacted to a growing chain of monomer units. For a more detailed discussion of the chemistry involved in the above synthetic approaches, see, for example, U.S. Pat. No. 5,436,327 at column 2, line 34, to column 4, line 36, which is incorporated herein by reference in its entirety.

An oligonucleotide probe may be, or may be capable of being, labeled with a reporter group, which generates a signal, or may be, or may be capable of becoming, bound to a support. Detection of signal depends upon the nature of the label or reporter group. Usually, the probe is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. Commonly, binding of the probes to the target is detected by means of a label incorporated into the target. Alternatively, the target may be unlabeled and a second probe nucleic acid labeled. Binding can be detected by separating the bound second probe or target from the free second probe or target and detecting the label. In one approach, a sandwich is formed comprised of one probe, which may be labeled, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target, allowing the target to hybridize to a surface-bound probe, washing away the unbound target and detecting the labeled target that remains. Direct detection of labeled target hybridized to surface-bound probes is particularly advantageous in the use of ordered arrays.

In one approach, cell matter is lysed, to release its DNA as fragments, which are then separated out by electrophoresis or other means, and then tagged with a fluorescent or other label. The DNA mix is exposed to an array of oligonucleotide probes, whereupon selective attachment to matching probe sites takes place. The array is then washed and the result of exposure to the array is determined. In this particular example, the array is imaged so as to reveal for analysis and interpretation the sites where attachment occurred.

The signal referred to above may arise from any moiety that may be incorporated into a molecule such as an oligonucleotide probe for the purpose of detection. Often, a label is employed, which may be a member of a signal producing system. The label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation and (v) a specific polynucleotide sequence or recognition sequence that can act as a ligand such as for a repressor protein, wherein in the latter two instances the oligonucleotide primer or repressor protein will have, or be capable of having, a reporter molecule and so forth. The reporter molecule can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like.

The signal may be produced by a signal producing system, which is a system that generates a signal that relates to the presence or amount of a target polynucleotide in a medium. The signal producing system may have one or more components, at least one component being the label. The signal producing system includes all of the reagents required to produce a measurable signal. The signal producing system provides a signal detectable by external means, by use of electromagnetic radiation, desirably by visual examination. Signal-producing systems that may be employed in the present invention are those described more fully in U.S. Pat. No. 5,508,178, the relevant disclosure of which is incorporated herein by reference.

One aspect of the present invention is an addressable array comprising a support having a surface, a spot on the surface having bound thereto an oligonucleotide probe specific for a target nucleic acid sequence and at least one spot on the surface having bound thereto a cross-hybridization oligonucleotide probe wherein the cross-hybridization oligonucleotide probe measures the extent of the occurrence of a cross-hybridization event of a predetermined probability between an interfering nucleic acid sequence and the oligonucleotide probe specific for a target nucleic acid sequence. The probes are employed in an effective amount, namely, an amount that will yield the desired result such as detection of the target nucleic acid sequence.

A method for detecting a target nucleic acid sequence comprises contacting a medium suspected of containing the target nucleic acid sequence with the above addressable array and determining a result of the contacting. The result indicates the presence or absence of the target nucleic acid sequence in the medium. The result may be determined by examining the array for the presence of a hybrid of the target nucleic acid sequence and the oligonucleotide probe specific for the target nucleic acid sequence. The presence of the hybrid indicates the presence of the target nucleic acid sequence in the medium. In one approach the target nucleic acid sequence is labeled and the result is determined by examining the array for the presence of signal associated with the label, the signal being related to the presence of the hybrid. One aspect of the invention is the product of the above method, namely, the assay result, which may be evaluated at the site of the testing or it may be shipped to another site for evaluation and communication to an interested party.

The methods of the present invention are preferably carried out at least in part with the aid of a computer. For example, an IBM® compatible personal computer (PC) may be utilized. The computer is driven by software specific to the methods described herein. In one aspect a computer based method may comprise the following: Under computer control a cross-hybridization oligonucleotide probe is identified based on the target nucleic acid sequence. The cross-hybridization oligonucleotide probe measures the extent of the occurrence of a cross-hybridization event having a predetermined probability. Under computer control cross-hybridization results are determined employing the cross-hybridization oligonucleotide probe and target-specific oligonucleotide probe. A selection or rejection of the target-specific oligonucleotide probe for the set based on the cross-hybridization results is carried out under computer control. The output from the results of the above may be directed under computer control to a manufacturing apparatus for production of various oligonucleotide probes identified in accordance with the present invention.

The preferred computer hardware capable of assisting in the operation of the methods in accordance with the present invention involves a system with at least the following specifications: Pentium® processor or better with a clock speed of at least 100 MHz, at least 32 megabytes of random access memory (RAM) and at least 80 megabytes of virtual memory, running under either the Windows 95 or Windows NT 4.0 operating system (or successor thereof).

As mentioned above, software that may be used to carry out the methods may be, for example, Microsoft Excel or Microsoft Access, suitably extended via user-written functions and templates, and linked when necessary to stand-alone programs that perform homology searches or sequence manipulations. Examples of software or computer programs used in assisting in conducting the present methods may be written, preferably, in Visual BASIC, FORTRAN and C++, as exemplified below in the Examples. It should be understood that the above computer information and the software used herein are by way of example and not limitation. The present methods may be adapted to other computers and software. Other languages that may be used include, for example, PASCAL, PERL or assembly language.

As indicated above, a computer program may be utilized to carry out the above method steps. The computer program provides for (i) input of target nucleic acid sequence information, (ii) efficient algorithms for computation of cross-hybridization oligonucleotide probes, (iii) efficient, versatile mechanisms for filtering sets of oligonucleotide sequences based on parameter values, (iv) mechanisms for measurement of cross-hybridization results employing cross-hybridization oligonucleotide probes and target-specific oligonucleotide probes, and (v) mechanisms for outputting the results to provide for selecting or rejecting a particular target-specific oligonucleotide probe for the set of such probes in accordance with the method of the present invention in a versatile, machine-readable or human-readable form. As mentioned above, the output may be directed to a manufacturing apparatus for synthesizing oligonucleotides.

Another aspect of the present invention is a computer program product comprising a computer readable storage medium having a computer program stored thereon which, when loaded into a computer, selects a set of target-specific oligonucleotide probes for use in analyzing a target nucleic acid sequence. The computer program performs steps comprising (a) identifying under computer control a cross-hybridization oligonucleotide probe based on the target nucleic acid sequence wherein the cross-hybridization oligonucleotide probe measures the extent of the occurrence of a cross-hybridization event having a predetermined probability, (b) determining under computer control cross-hybridization results employing the cross-hybridization oligonucleotide probe and target-specific oligonucleotide probe and (c) selecting or rejecting under computer control the target-specific oligonucleotide probe for the set based on the cross-hybridization results.

Any of the steps of the methods of the present invention can be executed on a suitable computer system. The computer system may be programmed from a computer readable storage medium that carries code for the system to execute the steps required of it. The computer readable storage medium may comprise, for example, magnetic storage media such as optical disc, optical tape, or machine readable bar code, solid state electronic storage devices such as random access memory (RAM), or read only memory (ROM), or any other physical device or medium that might be employed to store a computer program. It will also be understood that computer systems of the present invention can include the foregoing programmable systems and/or hardware or hardware/software combinations that can execute the same or equivalent steps.

The computer based method may be carried out by using the following exemplary computer system. Input means is provided for introducing a target nucleotide sequence into the computer system. The input means may permit manual input of the target nucleic acid sequence. The input means may also be a database or a standard format file such as GenBank. Also included is means for determining a cross-hybridization oligonucleotide probe based on the target nucleic acid sequence wherein the cross-hybridization oligonucleotide probe measures the extent of the occurrence of a cross-hybridization event having a predetermined probability. Suitable means is a computer program or software, which also provides memory means for determining and storing cross-hybridization results employing the cross-hybridization oligonucleotide probe and target-specific oligonucleotide probe. The computer system further comprises means for controlling the computer system to select or reject the target-specific oligonucleotide probe for the set based on the cross-hybridization results. Suitable means is a computer program or software such as, for example, Microsoft® Excel spreadsheet, Microsoft® Access relational database or the like, which also provides memory means for storing selection results. The computer system also comprises means for outputting data relating to the selection results. Such means may be machine readable or human readable and may be software that communicates with a printer, electronic mail, another computer program, and the like. One particularly attractive feature of the present invention is that the outputting means may communicate directly with software that is part of an oligonucleotide synthesizer. In this way the results of the method of the present invention may be used directly to provide instruction for the synthesis of the desired oligonucleotides.

Kits of the Invention

Another aspect of the present invention relates to kits useful for conveniently performing a method in accordance with the invention. To enhance the versatility of the subject invention, the reagents can be provided in packaged combination, in the same or separate containers, so that the ratio of the reagents provides for substantial optimization of the method. The reagents may each be in separate containers or various reagents can be combined in one or more containers depending on the cross-reactivity and stability of the reagents.

In one embodiment a kit comprises an oligonucleotide probe that is specific for the target nucleic acid sequence and a cross-hybridization oligonucleotide probe based on a candidate target-specific oligonucleotide probe for the target nucleic acid sequence. The target-specific oligonucleotide probes may comprise a label. The cross-hybridization oligonucleotide probe measures the occurrence of a cross-hybridization event of predetermined probability between an interfering nucleic acid sequence and the oligonucleotide probe specific for the target nucleic acid sequence. In one aspect the cross-hybridization results obtained with the cross-hybridization oligonucleotide probe, which may be a single probe or a set comprising a minimum number of such probes, are substantially the same as an average of results obtained with the full set of cross-hybridization oligonucleotide probes.

The kit can further include other separately packaged reagents for conducting the method as well as ancillary reagents and so forth. The relative amounts of the various reagents in the kits can be varied widely to provide for concentrations of the reagents that substantially optimize the reactions that need to occur during the present method. Under appropriate circumstances one or more of the reagents in the kit can be provided as a dry powder, usually lyophilized, including excipients, which on dissolution will provide for a reagent solution having the appropriate concentrations for performing a method in accordance with the present invention. The kit can further include a written description of a method in accordance with the present invention as described above.

The reagents, methods and kits of the invention are useful for, among others, mutation detection, mutation identification, polymorphism analysis, genotyping, de novo sequencing, re-sequencing, gene expression profiling, cDNA clustering and the like.

It should be understood that the above description is intended to illustrate and not limit the scope of the invention. Other aspects, advantages and modifications within the scope of the invention will be apparent to those skilled in the art to which the invention pertains. The invention has application to biopolymers in general such as, for example, polynucleotides, poly (amino acids), e.g., proteins and peptides, and the like. Factors in the application of the present invention to a particular biopolymer include the ability of the biopolymer to show homology phenomena that can be studied and the availability of a reasonable method for scoring such homology phenomena. In application of the present invention to biopolymers in general the term "hybridizing" used herein would have the more general meaning of "binding" between biopolymers. The following examples are put forth so as to provide those of ordinary skill in the art with examples of how to make and use the method and products of the invention, and are not intended to limit the scope of what the inventors regard as their invention.

EXAMPLES

The invention is demonstrated further by the following illustrative examples. Parts and percentages are by weight unless indicated otherwise. Temperatures are in degrees centigrade (° C.).

Example 1

Evaluation of the Predictive Value of Homologous Cross-hybridization Control Probes Using a Model System The predictive ability of cross-hybridization control probes designed by a homologous probe method in accordance with the present invention was examined in a model system based on 3 homologous yeast genes. Control probes based on mismatched bases or deletions at a central probe position were also evaluated. The 3 yeast genes chosen are listed in Table 1.

TABLE 1

Yeast genes used in the model system

| Yeast Genome Standard Name | Gene Locus Name | SEQ ID No: | Gene Product & Function | Role in Model System (label) |
|---|---|---|---|---|
| YFL039c | ACT1 | 31 | β-actin, cytoskeleton | gene-specific target (Cy3) |
| YHR129c | ARP1 | 32 | actin-related protein, cytoskeleton | cross-hybridization target (Cy5) |
| YDL029w | ARP2 | 33 | actin-related protein, cytoskeleton | cross-hybridization target (Cy5) |

Sequences for all 3 ORF's were obtained via the database search facility of the Saccharomyces Genome Database, whose universal resource locator (URL) on the World-Wide Web is http://genome-www.stanford.edu/cgi-bin/SGD/search.

Templates for production of labeled target cRNA were produced using primers compatible with the universal yeast ORF PCR primer/template system sold by Research Genetics (Huntsville, Ala.). The universal reverse PCR primer sequence was modified from the manufacturer's recommended sequence by addition of a T7 RNA polymerase promoter to the 5' end of the primer. Primers were custom-synthesized by Operon, Inc. (Alameda, Calif.). The primer sequences were

GGAATTCCAGCTGACCACCATG (SEQ ID NO: 34)

TGAATTGTAATACGACTCACTATAGG-
GAGGATCCCCGGGAATTGCCATG (SEQ ID NO: 35)

introduced at position 12 (near the center of the 25-mer probe). The original, sequence-specific probe names do not contain the character strings "HOM", "DL" or "MM", and are shown in italics.

TABLE 2

Probe sequences

| Probe Name | Sequence | SEQ ID NO: |
|---|---|---|
| YFL039C-25-0413 | CCGTTTTGTCCTTGTACTCTTCCGG | 36 |
| YFL039C_HOM-25-0413 | ACGTTTTAACTTTGCACTCTTCCGC | 37 |
| YFL039C_DL12-24-y0413 | CCGTTTTGTCCTGTACTCTTCCGG | 38 |
| YFL039C_MM1012-25-0413 | CCGTTTTGTCCATGTACTCTTCCGG | 39 |
| YFL039C_MM2012-25-0413 | CCGTTTTGTCCGTGTACTCTTCCGG | 40 |
| YFL039C_MM3012-25-0413 | CCGTTTTGTCCCTGTACTCTTCCGG | 41 |
| YFL039C-25-0461 | ATTCCGGTGATGGTGTTACTCACGT | 42 |
| YFL039C_HOM-25-0461 | ATTCCGGTGACGGTGTTACTCATAT | 43 |
| YFL039C_DL12-24-0461 | ATTCCGGTGATGTGTTACTCACGT | 44 |
| YFL039C_MM1012-25-0461 | ATTCCGGTGATCGTGTTACTCACGT | 45 |
| YFL039C_MM2012-25-0461 | ATTCCGGTGATTGTGTTACTCACGT | 46 |
| YFL039C_MM3012-25-0461 | ATTCCGGTGATAGTGTTACTCACGT | 47 |
| YFL039C-25-0783 | GTTCCATCCTTCTGTTTTGGGTTTG | 48 |
| YFL039C_HOM-25-0783 | ATTCCATCGTTCTGTTCCAGATTTG | 49 |
| YFL039C_DL12-24-0783 | GTTCCATCCTTTGTTTTGGGTTTG | 50 |
| YFL039C_MM1012-25-0783 | GTTCCATCCTTGTGTTTTGGGTTTG | 51 |
| YFL039C_MM2012-25-0783 | GTTCCATCCTTATGTTTTGGGTTTG | 52 |
| YFL039C_MM3012-25-0783 | GTTCCATCCTTTTGTTTTGGGTTTG | 53 |
| YFL039C-25-0955 | GCTTTGGCTCCATCTTCCATGAAGG | 54 |
| YFL039C_HOM-25-0955 | TCTTTGGCTTCATCTTTCATGAATT | 55 |
| YFL039C_DL12-24-0955 | GCTTTGGCTCCTCTTCCATGAAGG | 56 |
| YFL039C_MM1012-25-0955 | GCTTTGGCTCCTTCTTCCATGAAGG | 57 |
| YFL039C_MM2012-25-0955 | GCTTTGGCTCCCTCTTCCATGAAGG | 58 |
| YFL039C_MM3012-25-0955 | GCTTTGGCTCCGTCTTCCATGAAGG | 59 |
| YFL039C-25-0983 | AGATCATTGCTCCTCCAGAAAGAAA | 60 |
| YFL039C_HOM-25-0983 | AGATTATAGCCCCTTCAGAAAGAAA | 61 |
| YFL039C_DL12-24-0983 | AGATCATTGCTCTCCAGAAAGAAA | 62 |
| YFL039C_MM1012-25-0983 | AGATCATTGCTGCTCCAGAAAGAAA | 63 |
| YFL039C_MM2012-25-0983 | AGATCATTGCTACTCCAGAAAGAAA | 64 |
| YFL039C_MM3012-25-0983 | AGATCATTGCTTCTCCAGAAAGAAA | 65 |
| YFL039C-25-1019 | GGATTGGTGGTTCTATCTTGGCTTC | 66 |
| YFL039C_HOM-25-1019 | GGAATGGCGTTCTATCTTTGCTTC | 67 |
| YFL039C_DL12-24-1019 | GGATTGGTGGTCTATCTTGGCTTC | 68 |
| YFL039C_MM1012-25-1019 | GGATTGGTGGTACTATCTTGGCTTC | 69 |
| YFL039C_MM2012-25-1019 | GGATTGGTGGTGCTATCTTGGCTTC | 70 |
| YFL039C_MM3012-25-1019 | GGATTGGTGGTCCTATCTTGGCTTC | 71 |

Labeled cRNA targets were produced by transcribing PCR products using T7-RNA polymerase (Epicentre, Madison, Wis.) and a nucleotide triphosphate mixture containing Cy3- or Cy5-labeled CTP (New England Biolabs, Boston, Mass.). Labeled targets were characterized by gel electrophoresis, and found to be full-length.

The results of survey array experiments were used to demonstrate the locations of several oligonucleotide probes that efficiently detected the YFL039c cRNA target. Briefly, an array was constructed that was a survey set of oligonucleotide probes equally spaced for the target sequence. The arrays were used to study hybridization of target sequence to the array and to study the hybridization of homologous sequences to the array. An in situ-synthesized nucleotide probe array was designed and manufactured based on these previously identified probes. The experimental probes placed on the array are summarized in Table 2 below. The probe naming convention used distinguishes probes designed on the basis of homology (HOM), probes from which one base has been deleted (DL) and probes containing a base that is mismatched with respect to the target sequence (MM). All deletions and mismatches were Each probe sequence was repeated 15 or 16 times on the array. The yeast ORF's that were the sources of the cross-hybridization probes designed on the basis of homology are listed in Table 3 below. The probes represent the best symbolic matches found for each target specific probe in the entire set of recognized yeast ORF's.

TABLE 3

Sources of homologous probes

| Target-Specific Probe | Source of Homologous Probe (Standard ORF Name) | Position of Homologous Probe in ORF |
|---|---|---|
| YFL039C-25-0413 | YKR097w | 683 |
| YFL039C-25-0461 | YDL029w | 470 |
| YFL039C-25-0783 | YGL019w | 79 |
| YFL039C-25-0955 | YCL028w | 535 |
| YFL039C-25-0983 | YHR129c | 1013 |
| YFL039C-25-1019 | YNR041c | 544 |

The array also contained 30 copies of a positive control sequence (Pro25G) for the purpose of hybridizing to the Cy3- and Cy5-labeled versions of its Watson-Crick complement, TAR25C. The control targets were synthesized by Operon (Alameda, Calif.); their sequences are 5'Cy3-GGATACACTGACCAGCTACGATGAT (Cy3-TAR25C: SEQ ID NO.: 72)
5'Cy5-GGATACACTGACCAGCTACGATGAT (Cy5-TAR25C: SEQ ID NO.: 73)

The arrays were hybridized to a model target mixture, at 37° C., overnight. The base buffer was 6× SSPE (900 mM sodium chloride/ 60 mM sodium phosphate/ 6 mM EDTA, pH7.5). The hybridization mixture was assembled by mixing the following components in the order given:

| Initial Concentration | Amount | Final Concentration |
|---|---|---|
| 12x SSPE containing 2% w/v Triton X-100 nuclease-free, sterile water | 125.0 µl | 6x |
| | 79.0 µl | |
| 10 mg/ml heat-denatured herring sperm DNA | 2.5 µl | 0.1 mg/ml |
| bovine serum albumin, 10 mg/ml | 25.0 µl | 10 nM |
| sodium dodecyl sulfate, 10% w/v | 2.5 µl | 10 nM |
| 10 nM 5'Cy3-TAR25C | 5.0 µl | 1 nM |
| 10 nM 5'Cy5-TAR25C | 5.0 µl | 1 nM |
| 5 nM Cy3-YFL039c cRNA | 5.0 µl | 100 pM |
| 50 nM Cy5 YDL029w cRNA | 0.5 µl | 100 pM |
| 50 nM CyS YHR129c cRNA | 0.5 µl | 100 pM |
| | 250.0 µl | |

Bovine serum albumin (BSA) was obtained from Sigma Chemical Company, Saint Louis, Mo. (product No A7906). Herring sperm DNA was obtained from Promega, Madison, Wis. (Product No. D181B), and was denatured by heating to 95° C. for 5 minutes, then cooling rapidly, prior to use. All other reagents were obtained from Amresco, Solon, Ohio. The cRNA targets were not fragmented before hybridization.

After hybridization, the array was washed in 0.1× SSPE containing 0.005% w/v Triton X-100 at 37° C. for 15 minutes. The array was rinsed for 10 seconds in 0.1× SSPE containing 0.005% w/v Triton X-100, blown dry with filtered nitrogen gas, and stored in the dark. The array was scanned dry for both Cy3 and Cy5 fluorescence using an Avalanche laser scanner (Molecular Dynamics, Sunnyvale, Calif.). The array images were quantitated by integrating the measured intensity over a 150 µm diameter disk centered on each ~200 µm diameter feature. Background signal in each color channel was determined by averaging the signals measured from non-probe regions near array features and was subtracted from the integrated signals measured in the same color channel. The net signals were grouped according to surface-bound probe, and net signals for repeated measurements by the same probe sequence were averaged. Finally, to produce the result from the array analysis, the Cy5 averaged net signals were corrected for the different quantum yields and detection efficiencies of Cy3 and Cy5 by multiplying each average net Cy5 signal by the ratio of the average net signal from the Cy3-labeled TAR25C control oligonucleotide to the average net signal from the Cy5-labeled TAR25C control oligonucleotide. Since the two versions of the control oligonucleotide were present at equal concentrations, their corrected signals should be equal; multiplication by the described ratio equalizes the control oligonucleotide signals.

The experiment was designed to allow independent determination of target-specific hybridization and cross-hybridization by labeling the intended target and the potentially cross-hybridizing targets with spectrally distinguishable fluorophores. The two potentially cross-hybridizing targets chosen, YHR129c (ARP1) and YDL029w (ARP2) are 61% and 62% identical (respectively) to the specific target, YFL039c (ACT1). In addition, the homologous probes identified by symbolic matching of the sequences of probes YFL039C-25-983 and YFL039C-25-461 are derived from these two ORF's (see Table 3).

Table 4 below reports the Cy3 (target-specific) and Cy5 (cross-hybridization) signals measured for each YFL039c target-specific probe along with the Cy3/Cy5 ratio for that probe. Since the Cy3 signal is purely target-specific and the Cy5 signal arises purely from cross-hybridization, the ratio indicates the specificity of the hybridization, with larger ratios indicating greater specificity.

TABLE 4

Target-specific probe results

| Probe Name | Average Net Cy3 Signal | Corrected, Average Net Cy5 Signal | Cy3/Cy5 Ratio |
|---|---|---|---|
| YFL039C-25-0413 | 13,168.1 | 370.5 | 35.55 |
| YFL039C-25-0461 | 3,834.2 | 2,490.5 | 1.54 |
| YFL039C-25-0783 | 19,052.5 | 677.9 | 28.11 |
| YFL039C-25-0955 | 7,589.5 | 257.0 | 29.53 |
| YFL039C-25-0983 | 9,301.8 | 338.3 | 27.50 |
| YFL039C-25-1019 | 1,305.8 | 1,858.7 | 0.70 |

It may be seen from Table 4 that hybridization to probes YFL039C-25-0413, -0783, -0955 and -0983 was specific, while hybridization to probes YFL039C-25-0461 and -1019 was not.

The corresponding predictions of cross-hybridization control probes designed on the basis of homology are summarized in Table 5. In Table 5, the Cy3 and corrected Cy5 signals have been added together in order to simulate the results of an experiment performed with a single label (i.e., an experiment in which target-specific hybridization and cross-hybridization cannot be distinguished on the basis of different labels). This provides a model for the situation that would occur during probe optimization using a complex RNA mixture bearing a single label (i.e. samples derived from real cells). The ratio of the homology probe signal to the target-specific probe signal (HP/TSP) is the same as the "$S_b/S_a$" ratio defined in equation 14 of the preceding text. Finally, the names of the homologous probe sources whose targets were included in the experiment (YDL029w and YHR129c) are shown in italics.

TABLE 5

Cross-hybridization probe predictions

| Target-Specific Probe Name | Cy3 Signal + Corrected Cy5 Signal | | HP/TSP Ratio | Homo-logous Probe Source |
|---|---|---|---|---|
| | Target-Specific Probe (TSP) Signal | Homologous Probe (HP) Signal | | |
| YFL039C-25-0413 | 13,538.6 | 5.2 | 0.04% | YKR097w |
| YFL039C-25-0461 | 6,324.8 | 4,529.4 | 71.61% | YDL029w |
| YFL039C-25-0783 | 19,730.4 | 28.3 | 0.14% | YGL019w |
| YFL039C-25-0955 | 7,846.5 | 1,087.2 | 13.86% | YCL028w |
| YFL039C-25-0983 | 9,640.1 | 5,558.6 | 57.66% | YHR129c |
| YFL039C-25-1019 | 3,164.5 | 46.6 | 1.47% | YNR041c |

The HP/TSP ratios in Table 5 predict that probe YFL039C-25-0461 is likely to show low specificity. This prediction is confined by the specificity data (Table 4). The HP/TSP ratios also predict that probe YFL039C-25-0983 might not be specific. This prediction was not observed. However, the observation is in keeping with the model put forward in the preceding text: higher HP/TSP ratios only indicate that there may be a problem. Further experiments are needed to confirm that cross-hybridization really does occur.

The HP/TSP ratios in Table 5 also correctly predicted the observed high specificities of probes YFL039C-25-0413, YFL039C-25-0783 and YFL039C-25-0955. However, the ratios did not predict the observed low specificity of probe YFL039C-25-1019 (see Table 4). Fortuitously, the model system used in this experiment makes it possible to understand the reason for this failure.

Because there are only two RNA targets in the system that are labeled with Cy5 (YDL029w and YHR129c cRNA), the observed cross-hybridization to probe YFL039C-25-1019 must be derived from one or both of these targets. In order to determine if our symbolic match-scored homology algorithm might have missed an important homology between YFL039C-25-1019 and a portion of one of the cross-hybridization targets, we searched the yeast genome for homologues to YFL039C-25-1019 using the Wu BLAST2 facility described previously. This search yielded an unanticipated result: the best match found by Wu BLAST2 to YFL039c-25-1019 was YHR129c-25-1049, which is contained within one of the two cross-hybridization targets included in the experiment. The alignments of the target-specific probe, the homologous probe found by Wu BLAST2 and the homologous probe found by symbolic matching are shown below. Bases that are the same in all three sequences are shown in bold. Bases that match in at least two sequence s are underlined. Bases that do not match the corresponding base in YFL039c-25-1019 are italicized.

|  | (SEQ ID NO:66) |
| --- | --- |
| YFLO39c-25-1019 | GGATTGGTGGTTCTATCTTGGCTTC |

|  | (SEQ ID NO:74) |
| --- | --- |
| YHR129c-25-1049 | GGATTGGTGGTTCTATT*TT*AA*C*GGG |

|  | (SEQ ID NO:67) |
| --- | --- |
| YFLO39C_HOM-25-1019 | GGAATGGGCGTTCTATCTTTGCTTC |

The reason that Wu BLAST2 found a different best homologous probe may be seen from the above alignment. The symbolic matching homology search method used to design the homologous probe does not take into account the location or distribution of mismatched bases. In contrast, Wu BLAST2 imposes a penalty for gaps or mismatches in alignments and gives preference to homologues with longer contiguous runs of matching sequence. Such runs give rise to stronger binding of mismatched sequences. A contiguous run of at least about 15 nucleotides should be viewed as an identifying factor for a homologous probe to an interfering sequence having a high potential for interfering in the determination of a target polynucleotide sequence. It is evident that using Wu BLAST2 to design the homologous probes would have resulted in the selection of YHR129c-25-1049 as the control probe for YFL039c-25-1019, and in such a circumstance the observed cross-hybridization would have been correctly predicted. Thus, the results support the principle of the present invention that improvements in the scoring of homologies will lead to improvements in the performance of homology-based cross-hybridization control probes.

The conclusion that the homology scoring acheme influences the performance of cross-hybridization control probes designed on the basis of homology is further supported by the results of Wu BLAST2 searches of the yeast genome for homologues of probes YFL039C-25-0461 (cross-hybridization predicted, but not observed). and YFL039C-25-0983 (cross-hybridization predicted, but not observed). The best homologue of YFL039C-25-0461 found by Wu BLAST2 is the same as the best homologue found by symbolic matching. However, the best homologue to YFL039C-25-0983 found by Wu BLAST2 is different. An alignment of YFL039C-25-0983 to the Wu BLAST2 match (YPR040W-23-0290) and the symbolic match (YFL039C_HOM-25-0983) is shown below. Bases that are the same in all three sequences are emboldened. Bases that match in at least two sequences are underlined. Bases that do not match the corresponding base in YFL039c-25-0983 are italicized. Gaps are denoted by dashes.

|  | (SEQ ID NO:60) |
| --- | --- |
| YFL039C-25-0983 | AGATCATTGCTCCTCCAGAAAGAAA |

|  | (SEQ ID NO:61) |
| --- | --- |
| YFL039C_HOM-25-0983 | AGATT*AT*AGC*CCCT*TCAGAAAGAAA |

|  | (SEQ ID NO:75) |
| --- | --- |
| YPR040W-23-0290 | GGACCAT--CTCCTCCAGAAAGAAG |

The homologous sequence identified by symbolic matching intersperses mismatches throughout the center of the probe, while the sequence identified by Wu BLAST2 contains a longer contiguous match at the center of the probe, and concentrates mismatches near the end. Thus, the data suggest that Wu BLAST2 may be a preferred algorithm than symbolic matching for identifying cross-hybridization control probes.

It should be noted that this observation is a basis for designing oligonucleotide probes for detecting or detecting and distinguishing related sequences such as sequences that are specific to target polynucleotides derived from individual members of sets of homologous genes. The following explanation assumes that an experimenter wishes to detect targets derived from homologous genes. The targets may be mixed together in one sample (for example, the yeast ACT1, ARP1 and ARP2 genes of the present example) or may never occur in the same sample (for example, homologous genes from different species). The explanation further assumes that the labeled target polynucleotides are the complements of mRNA sequences (cDNA or cRNA), since this is the target strand generated by most target labeling methods. In this case, candidate probes are simply sub-sequences generated by parsing the gene coding sequence (see, for example, Table 2). However, this explanation is easily generalized by one skilled in the art to apply to labeled target nucleotides derived from either strand of a gene.

In the method first oligonucleotide probes that are sensitive to a target polynucleotide derived from a first related sequence are identified. Second oligonucleotide probes that are intended to detect a target polynucleotide derived from a second related sequence are also identified. The second oligonucleotide probes are homologous probes derived from the second related sequence that correspond to the first oligonucleotide probes derived from the first related sequence. The second oligonucleotide probes are scored based on the degree of homology between the second and first probes. A defined range of second probe scores is indicative of oligonucleotide probes having a predetermined likelihood to cross-hybridize to a target polynucleotide derived from the first related sequence, e.g., those that are least likely to cross-hybridize. It should be noted that scoring criteria differ depending on whether the related sequences are in the same sample or in different samples such as samples from the same species or from different species. Where the related sequences are in different samples, e.g., from different species, the higher the scores obtained above, the more likely there will be cross-hybridization. However, since the samples are from different species, cross-hybridization will not matter. In the case of target polynucleotides derived from related sequences in the same sample, e.g., from the same species, the symbolic match scores between the first and second probes should be high but the mismatches should be distributed so that the thermodynamic score or the score from the gapped BLAST approach should be low. In a next step of the method, the second oligonucleotide probes are selected on the basis of their scores from above and are experimentally evaluated for their performance. For example, probe YFL039C-25-0983 is a good probe for distinguishing a target polynucleotide derived from YFL039c from a target polynucleotide derived from its homologue YHR129c, and its specificity can be predicted on the basis of the observation that the mismatches between the probe sequence and its homologue derived from YHR129c are well distributed across the center of the sequence.

Example 2

Evaluation of the Predictive Value of Mismatch and Deletion Cross-hybridization Control Probes Using a Model System The data for mismatch and deletion control probes included in the experiment of Example 1 are displayed in Table 6 below. The average of the signals produced by the three mismatch probes derived from each target-specific probe is also shown. Three facts are apparent from Table 6. First, the signal generated by both the mismatch and deletion probes is dominated by hybridization to the intended target. Second, the average mismatch signals and deletion probe signals are strongly correlated; a least-squares analysis constrained to include the origin yields a slope of 0.92 (units: deletion signal/average mismatch signal) and a coefficient of determination ($r^2$) of 0.91. Finally, in this system, under these conditions, hybridization to mismatched probes is a poor predictor of cross-hybridization potential. This last result is rather surprising, given that the use of such probes is currently the standard method of cross-hybridization control. This unexpected result emphasizes the advantage of designing cross-hybridization control probes on the basis of homology in accordance with the present invention.

Mismatch probes have other uses such as, for example, in mutational scanning. The above experiments show the equivalence of the performance of mismatch control probes and deletion probes. Accordingly, in accordance with another embodiment of the present invention, deletion probes may be used for mutational scanning. The expected signature of a mutation in the hybridization target is a deletion probe signal:target-specific signal of about 1, versus a ratio less than about 0.6 for a non-mutant target. Thus, the correspondence between deletion and mismatch probes can be used to improve the efficiency of mutational scanning, since only half as many probes are needed, compared to the conventional approach of tiling all 4 possible bases at a given position.

Thus, in the above embodiment of the present invention, differences between an individual sequence and a known reference sequence can be detected such as in, for example, mutational scanning. A labeled individual sequence, a surface bound reference oligonucleotide probe based on the known reference sequence and a set of surface bound deletion oligonucleotide probes are combined under hybridization conditions. The set of deletion oligonucleotide probes is prepared by a process comprising deleting nucleotides at one or more positions in a set of oligonucleotide probes corresponding to the reference oligonucleotide. Hybridization ratios are determined for the set of deletion oligonucleotide probes with respect to the reference oligonucleotide probe. The hybridization ratios are related to the presence or absence of differences between the individual sequence and the reference sequence.

TABLE 6

Mismatch and deletion probe signals

| Probe Name | Average Net Cy3 Signal (Target-Specific) | Corrected, Average Net Cy5 Signal (Target-Specific) |
|---|---|---|
| YFL039C-25-0413 | 13,168.1 | 370.5 |
| YFL039C_DL12-24-0413 | 7,566.9 | 209.8 |
| YFL039C_MM1012-25-0413 | 7,346.5 | 195.8 |
| YFL039C_MM2012-25-0413 | 5,392.9 | 118.0 |
| YFL039C_MM3012-25-0413 | 6,313.8 | 194.6 |
| YFL039C-25-0413 MM average | 6,351.0 | 169.5 |
| YFL039C-25-0461 | 3,834.2 | 2,490.5 |
| YFL039C_DL12-24-0461 | 178.2 | 108.2 |
| YFL039C_MM1012-25-0461 | 187.3 | 124.2 |
| YFL039C_MM2012-25-0461 | 147.1 | 155.9 |
| YFL039C_MM3012-25-0461 | 145.1 | 158.4 |
| YFL039C-25-0461 MM average | 159.8 | 146.1 |
| YFL039C-25-0783 | 19,052.5 | 677.9 |
| YFL039C_DL12-24-0783 | 6,064.3 | 196.5 |
| YFL039C_MM1012-25-0783 | 5,611.0 | 173.3 |
| YFL039C_MM2012-25-0783 | 6,726.2 | 202.3 |
| YFL039C_MM3012-25-0783 | 9,208.6 | 281.4 |
| YFL039C-25-0783 MM average | 7,182.0 | 219.0 |
| YFL039C-25-0955 | 7,589.5 | 257.0 |
| YFL039C_DL12-24-0955 | 3,427.8 | 161.6 |
| YFL039C_MM1012-25-0955 | 4,929.9 | 206.3 |
| YFL039C_MM2012-25-0955 | 2,677.9 | 88.9 |
| YFL039C_MM3012-25-0955 | 4,272.7 | 138.3 |
| YFL039C-25-0955 MM average | 3,960.1 | 144.5 |
| YFL039C-25-0983 | 9,301.8 | 338.3 |
| YFL039C_DL12-24-0983 | 378.4 | 23.6 |
| YFL039C_MM1012-25-0983 | 705.9 | 35.4 |
| YFL039C_MM2012-25-0983 | 822.7 | 118.7 |
| YFL039C_MM3012-25-0983 | 1,666.7 | 57.4 |
| YFL039C-25-0983 MM average | 1,065.1 | 70.5 |
| YFL039C-25-1019 | 1,305.8 | 1,858.7 |
| YFL039C_DL12-24-1019 | 317.6 | 54.5 |
| YFL039C_MM1012-25-1019 | 590.0 | 77.3 |
| YFL039C_MM2012-25-1019 | 152.2 | 48.7 |
| YFL039C_MM3012-25-1019 | 462.5 | 47.2 |
| YFL039C-25-1019 MM average | 401.5 | 57.8 |

All publications and patent applications cited in this specification are herein incorporated by reference as if each individual publication or patent application where specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING

<160> NUMBER OF SEQ ID NOS: 75

<210> SEQ ID NO 1
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YER019W-1230: Probe derived from the 19th open
      reading frame (ORF) on the right arm of yeast
      chromosome 5. The ORF is on the Watson strand.
      Probe starts at nucleotide 1230.
<300> PUBLICATION INFORMATION:
<301> AUTHORS: Dietrich, F. S.
      Mulligan, J.
      Hennessy, K.
      et al.,
<302> TITLE: The nucleotide sequence of Saccharomyces cerevisiae
      chromosome V
<303> JOURNAL: Nature
<304> VOLUME: 387
<306> PAGES: 78-81
<307> DATE: 1997

<400> SEQUENCE: 1
ggtcgtgaca acgtttactg caaac                                          25

<210> SEQ ID NO 2
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YML018C-0226: Probe derived from the 18th ORF
      on the left arm of yeast chromosome 13.  The ORF is a
      Crick strand.  Probe starts at nucleotide 226.
<300> PUBLICATION INFORMATION:
<301> AUTHORS: Bowman, S.
      Churcher, C.
      Badcock, K.
      et al.,
<302> TITLE: The nucleotide sequence of Saccharomyces cerevisiae
      chromosome XIII
<303> JOURNAL: Nature
<304> VOLUME: 387
<306> PAGES: 90-93
<307> DATE: 1997

<400> SEQUENCE: 2
ggccgtgcaa acgttcaccg cgaac                                          25

<210> SEQ ID NO 3
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YER019W-25-0618:  Probe derived from the 19th
      ORF on the right arm of yeast chromosome 5.  The ORF
      is on the Watson strand.  The probe starts at
      nucleotide 618.  Probe is same as SEQ ID NO 18 and
      20.
<300> PUBLICATION INFORMATION:
<301> AUTHORS: Dietrich, F. S.
      Mulligan, J.
<302> TITLE: The nucleotide sequence of Saccharomyces cerevisiae
      chromosome V
<303> JOURNAL: Nature
<304> VOLUME: 387

```
<306> PAGES: 78-81
<307> DATE: 1997

<400> SEQUENCE: 3
gtccatccac ctccgttaag cgtgc                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Same as SEQ
      ID NO 3, 5-7, except position 12 in sequence is "v".
      The letter "v" means "wobble bases", or equimolar
      combinations of A, G & C.

<400> SEQUENCE: 4
gtccatccac cvccgttaag cgtgc                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:  Same as
      SEQ ID NO 4, except at feature location 12,  "v" is
      replaced with A.

<400> SEQUENCE: 5
gtccatccac caccgttaag cgtgc                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Same as SEQ
      ID NO 4, except at feature location 12,  "v" is G.

<400> SEQUENCE: 6
gtccatccac cgccgttaag cgtgc                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:  Same as
      SEQ ID NO 4, except at feature location 12,  "v" is C.

<400> SEQUENCE: 7
gtccatccac ccccgttaag cgtgc                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:  Same as
      SEQ ID NO 3 and 9-17, except at feature locations 12
      and 13 "v" and "d" are wobble codes defined in specification.

<400> SEQUENCE: 8
gtccatccac cvdcgttaag cgtgc                                              25

<210> SEQ ID NO 9
<211> LENGTH: 25
```

```
<212> TYPE: DNA
<213> ORGANISM: Artificial Sequence
<220> FEATURE:
<223> OTHER INFORMATION: Description of Artificial Sequence: Sane as
      SEQ ID NO 8, except at feature locations 12 and 13, "vd" is AA.

<400> SEQUENCE: 9
gtccatccac caacgttaag cgtgc                                              25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Same as
      SEQ ID NO  8, except at feature locations 12 & 13, "vd" is AT.

<400> SEQUENCE: 10
gtccatccac catcgttaag cgtgc                                              25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Same as
      SEQ ID NO 8, except at feature locations 12 & 13 the "vd" is AG.

<400> SEQUENCE: 11
gtccatccac cagcgttaag cgtgc                                              25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Same as
      SEQ ID NO  8, except at feature locations 12 & 13, "vd" is GA.

<400> SEQUENCE: 12
gtccatccac cgacgttaag cgtgc                                              25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Same as
      SEQ ID NO  8, except at feature locations 12 & 13, "vd" is GT.

<400> SEQUENCE: 13
gtccatccac cgtcgttaag cgtgc                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Same as
      SEQ ID NO  8, except at feature locations 12 & 13, "vd" is GG.

<400> SEQUENCE: 14
gtccatccac cggcgttaag cgtgc                                              25

<210> SEQ ID NO 15
<211> LENGTH: 25
<212> TYPE: DNA
```

```
<213> ORGANISM: Artificial Sequence
<220> FEATURE:
<223> OTHER INFORMATION: Description of Artificial Sequence:  Same as
      SEQ ID NO 8, except at feature locations 12 & 13, "vd" is CA.

<400> SEQUENCE: 15
gtccatccac ccacgttaag cgtgc                                          25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:  Same as
      SEQ ID NO 8, except at feature locations 12 & 13, "vd" is CT.

<400> SEQUENCE: 16
gtccatccac cctcgttaag cgtgc                                          25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:  Same as
      SEQ ID NO 8, except at feature locations 12 & 13, "vd" is CG.

<400> SEQUENCE: 17
gtccatccac ccgcgttaag cgtgc                                          25

<210> SEQ ID NO 18
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YER019W-25-0618 is the same as SEQ ID NO 3 and
      20.
<300> PUBLICATION INFORMATION:
<302> TITLE: The nucleotide sequence of Saccharomyces cerevisiae
      chromosome V
<303> JOURNAL: Nature
<304> VOLUME: 387
<306> PAGES: 78-81
<307> DATE: 1997

<400> SEQUENCE: 18
gtccatccac ctccgttaag cgtgc                                          25

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence:  feature is
      stem_loop from location 14 to 23.

<400> SEQUENCE: 19
gcacgcttaa cccggacttc tccccgtgga tggac                               35

<210> SEQ ID NO 20
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YER019W-25-0618, which is the same as SEQ ID NO
```

3 & 18.
<300> PUBLICATION INFORMATION:
<302> TITLE: The nucleotide sequence of Saccharomyces cerevisiae
      chromosome V
<303> JOURNAL: Nature
<304> VOLUME: 387
<306> PAGES: 78-81
<307> DATE: 1997

<400> SEQUENCE: 20
gtccatccac ctccgttaag cgtgc                                              25

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:  Same as
      SEQ ID NO 20, except  wobble code "n" is added at
      feature location 13.  "n" is defined in
      specification.

<400> SEQUENCE: 21
gtccatccac ctnccgttaa gcgtgc                                             26

<210> SEQ ID NO 22
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-0983: a probe derived from the 39th
      ORF on the left arm of yeast chromosome 6.  The ORF is
      on the Crick stand and the probe starts at
      nucleotide  983.  Similar to portion of SEQ ID NO
      31.
<300> PUBLICATION INFORMATION:
<302> TITLE: Analysis of the nucleotide sequence of chromosome VI
      from Saccharomyces cerevisiae
<303> JOURNAL: Nature Genet.
<304> VOLUME: 10
<306> PAGES: 261-268
<307> DATE: 1995

<400> SEQUENCE: 22
catccaagcc gttttgtcct tgtac                                              25

<210> SEQ ID NO 23
<211> LENGTH: 16
<212> TYPE: DNA
<213> ORGANISM: Saccharomyces cerevisiae
<220> FEATURE:
<221> NAME/KEY: source
<222> LOCATION: (1)..(16)
<223> OTHER INFORMATION: YCL045C-16-0065: Probe derived from the 45th
      ORF on the left arm of yeast chromosome 3.  The ORF is
      on the Crick strand and the probe starts at
      nucleotide 65.
<221> NAME/KEY: old_sequence
<222> LOCATION: (14)
<223> OTHER INFORMATION: Changed base.
<300> PUBLICATION INFORMATION:
<302> TITLE: The complete DNA sequence of yeast chromosome III
<303> JOURNAL: Nature
<304> VOLUME: 357
<306> PAGES: 38-46
<307> DATE: 1992

<400> SEQUENCE: 23
tccaagccgt tttttc                                                        16

```
<210> SEQ ID NO 24
<211> LENGTH: 16
<212> TYPE: DNA
<213> ORGANISM: Saccharomyces cerevisiae
<220> FEATURE:
<221> NAME/KEY: source
<222> LOCATION: (1)..(16)
<223> OTHER INFORMATION: YFR030W-16-1561:  Probe derived from the 30th
      ORG on the right arm of yeast chromosome 6.  The ORF
      is on the Watson strand and the probe starts at
      nucleotide 1561.
<221> NAME/KEY: old_sequence
<222> LOCATION: (15)
<223> OTHER INFORMATION: Changed base.
<300> PUBLICATION INFORMATION:
<302> TITLE: Analysis of the nucleotide sequence of chromosome VI
      from Saccharomyces cerevisiae
<303> JOURNAL: Nature Genet.
<304> VOLUME: 10
<306> PAGES: 261-268
<307> DATE: 1995

<400> SEQUENCE: 24
atccaagccg ttttct                                                     16

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:  Synthetic
      probe has wobble code "y" at feature location 15,
      which is defined in the specification as C+T.

<400> SEQUENCE: 25
atccaagccg ttttytc                                                    17

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: unsure,
      presented for sake of argument.

<400> SEQUENCE: 26
cgaatccgtt agcaaactga tgcatt                                          26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Same as SEQ
      ID NO. 26, except at feature location 22, G is replaced with C.

<400> SEQUENCE: 27
cgaatccgtt agcaaactga tccatt                                          26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Same as SEQ
      ID NO 27, except at feature location 22, A replaces C.

<400> SEQUENCE: 28
cgaatccgtt agcaaactga tacatt                                          26
```

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Same as
      SEQ ID NO 27 & 28, except at feature location 22, T
      replaces C and A, respectively.

<400> SEQUENCE: 29
cgaatccgtt agcaaactga ttcatt                                          26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Same as
      SEQ ID NO 27-29, except at feature locations 22-24,
      the nucleotides are TAC.

<400> SEQUENCE: 30
cgaatccgtt agcaaactga ttactt                                          26

<210> SEQ ID NO 31
<211> LENGTH: 1436
<212> TYPE: DNA
<213> ORGANISM: Saccharomyces cerevisiae
<220> FEATURE:
<221> NAME/KEY: source
<222> LOCATION: (1)..(1436)
<223> OTHER INFORMATION: YFL039C is a probe derived from the 39th ORF on
      the left arm of yeast chromosome 6.  The ORF is on
      the Crick strand.
<300> PUBLICATION INFORMATION:
<302> TITLE: Analysis of the nucleotide sequence of chromosome VI
      from Saccharomyces cerevisiae
<303> JOURNAL: Nature Genet.
<304> VOLUME: 10
<306> PAGES: 261-268
<307> DATE: 1995

<400> SEQUENCE: 31
atggattctg gtatgttcta gcgcttgcac catcccattt aactgtaaga agaattgcac      60
ggtcccaatt gctcgagaga tttctctttt acctttttt actatttttc actctcccat     120
aacctcctat attgactgat ctgtaataac cacgatatta ttggaataaa tagggcttg     180 aaatttggaa aaaaaaaaa actgaaatat tttcgtgata agtgatagtg atattcttct     240
tttatttgct actgttacta agtctcatgt actaacatcg attgcttcat tcttttttgtt   300 gctatattat atgtttagag gttgctgctt tggttattga taacggttct ggtatgtgta    360
aagccggttt tgccggtgac gacgctcctc gtgctgtctt cccatctatc gtcggtagac    420
caagacacca aggtatcatg gtcggtatgg gtcaaaaaga ctcctacgtt ggtgatgaag    480
ctcaatccaa gagaggtatc ttgactttac gttacccaat tgaacacggt attgtcacca    540
actgggacga tatggaaaag atctggcatc ataccttcta caacgaattg agagttgccc    600
cagaagaaca ccctgttctt ttgactgaag ctccaatgaa ccctaaatca acagagaaa     660 agatgactca aattatgttt gaactttca acgttccagc cttctacgtt tccatccaag     720
ccgttttgtc cttgtactct tccggtagaa ctactggtat tgttttggat tccggtgatg    780
gtgttactca cgtcgttcca atttacgctg gtttctctct acctcacgcc atttttgagaa   840 tcgatttggc cggtagagat ttgactgact acttgatgaa gatcttgagt gaacgtggtt    900

-continued

```
actctttctc caccactgct gaaagagaaa ttgtccgtga catcaaggaa aaactatgtt      960
acgtcgcctt ggacttcgaa caagaaatgc aaaccgctgc tcaatcttct tcaattgaaa     1020
aatcctacga acttccagat ggtcaagtca tcactattgg taacgaaaga ttcagagccc     1080
cagaagcttt gttccatcct tctgttttgg gtttggaatc tgccggtatt gaccaaacta     1140
cttacaactc catcatgaag tgtgatgtcg atgtccgtaa ggaattatac ggtaacatcg     1200
ttatgtccgg tggtaccacc atgttcccag gtattgccga agaatgcaa aaggaaatca     1260 ccgctttggc tccatcttcc atgaaggtca agatcattgc tcctccagaa agaaagtact     1320
ccgtctggat tggtggttct atcttggctt ctttgactac cttccaacaa atgtggatct     1380
caaaacaaga atacgacgaa agtggtccat ctatcgttca ccacaagtgt ttctaa        1436
```

<210> SEQ ID NO 32
<211> LENGTH: 1155
<212> TYPE: DNA
<213> ORGANISM: Saccharomyces cerevisiae
<220> FEATURE:
<221> NAME/KEY: source
<222> LOCATION: (1)..(1155)
<223> OTHER INFORMATION: YHR129C is a probe derived from the 139th ORF
    on the right arm of yeast chromosome 8. The ORF is
    on the Crick strand.
<300> PUBLICATION INFORMATION:
<302> TITLE: Complete nucleotide sequence of Saccharomyces
    cerevisiae chromosome VIII
<303> JOURNAL: Science
<304> VOLUME: 265
<306> PAGES: 2077-2082
<307> DATE: 1994

<400> SEQUENCE: 32

```
atggaccagc taagtgacag ctatgctttg tacaatcaac cggtagtgat cgacaatggt       60
tctgggatca taaaagcagg atttagtggt gaggaaaggc ctaaagcact ggaatattgt      120
ctcgtaggaa ataccaaata tgataaagtt atgctcgaag gtctgcaagg agatacattt      180
attggaaaca atgcccaaaa actgcgtgga ttattaaaat tacgatacccc cataaagcac    240 ggcgtggtgg aagattggga ttctatggaa ctaatatggt catatgtgtt aaatgaagtc     300
ctacagttgc aaaatatagg tgagcatcct ttattaatta cggaagcccc gatgaatcct     360
ttgaagaata gagagcagat ggctcaagta ttgttcgaga cctttgacgt atcggctttg     420
tacgtttcaa accctgctgt tctgtcatta tatgctagtg ggagaactac aggttgtgta     480
gttgactgtg gtgaaggata ctgtagcact gttcccatat atgacggctt tgcattacct     540
gcgtctatga tgaggatgga tattggagga gcagatatca cagagcagtt acaatttcaa     600
ctacggaaat cagctggtgt ttcgttgttt tccagcagtg aacgagagat tgttcgcacg     660
atgaaagaga agtttgtta tttggccaag aatattaaaa aggaagagga gaaatactta     720
caaggtactc aagatttaat ctcgacattc aaattgcccg acgggaggtg tatagaggtg     780
gggaatgatc gatatcgtgc tccagaaata ttattttcac ctcaaatcat cggcttaggg    840
tacgatggat tatctgatat gtgcatgcaa tctatttgga aagtcgatct ggatttaagg    900
aaacctttac tgtcatcgat aatcctaagt ggcggaacta caacgcttaa aggctttgga   960
gaccgaatgc tatgggattt ggaggcatta accaaaggaa catccaagat aaagattata    1020
gccccttcag aaagaaaata tactacatgg attggtggtt ctattttaac ggggttatct   1080 accttttcaaa gactttggac caaaaagtca gattggctag aggacagtac ccgtgttat    1140 tcgaacctaa tgtaa                                                     1155
```

<210> SEQ ID NO 33
<211> LENGTH: 1299
<212> TYPE: DNA
<213> ORGANISM: Saccharomyces cerevisiae
<220> FEATURE:
<221> NAME/KEY: source
<222> LOCATION: (1)..(1299)
<223> OTHER INFORMATION: YDL029W is a probe derived from the 29th ORF on
      the left arm of yeast chromosome 4. The ORF is on
      the Watson strand.
<300> PUBLICATION INFORMATION:
<302> TITLE: Complete DNA sequence of yeast chromosome IV
<303> JOURNAL: Nature
<304> VOLUME: 387
<306> PAGES: 75-78
<307> DATE: 1997

<400> SEQUENCE: 33

| | | | | | |
|---|---|---|---|---|---|
| atggacccac | ataatccaat | tggtatgttg | ttgatatttt | tagtgtttgt | ggaggcaatt    60 |
| gagctcggtg | ccccttttgg | ctttgcctct | tttgcatttt | agttctttta | cccctatatt   120 |
| attaatacta | accatctcga | tatagtcctt | gatcagggta | ctggtttcgt | caaaattggt   180 |
| cgtgctggcg | agaatttccc | agattacacg | tttccttcta | ttgttggtag | acccatcttg   240 |
| agggcggaag | aacgtgccag | cgttgctaca | ccattaaagg | acattatgat | tggtgatgag   300 |
| gcaagtgaag | ttcgctctta | tctgcaaata | tcttatccta | tggaaaacgg | tattattaag   360 |
| aattggacag | atatggaact | tctttgggat | tacgcctttt | tcgagcaaat | gaaactacca   420 |
| tccacctcca | acggtaagat | tttactaacg | gaacctccaa | tgaatccgct | gaaaaatagg   480 |
| gaaaaaatgt | gtgaggtaat | gttcgaaaaa | tacgattttg | gcggagttta | tgttgccatc   540 |
| caagctgttc | tagcattgta | cgcacaaggt | ttgtcttcag | gagtcgtcgt | cgattccggt   600 |
| gacggtgtta | ctcatatagt | cccagtttac | gaatctgtcg | ttttgagcca | cttaacaaga   660 |
| agattagatg | ttgcgggtag | agacgttact | aggcatttga | ttgatctgct | ttctcgtcgt   720 |
| ggttatgcat | ttaacagaac | tgcagatttc | gaaactgtgc | gtcagataaa | ggaaaaatta   780 |
| tgttatgttt | catatgattt | agacctagat | acaaaattgg | ctagagaaac | aaccgccctt   840 |
| gtggaatcgt | atgagttacc | agatggcagg | acaatcaaag | tgggacaaga | gagatttgaa   900 |
| gcaccagaat | gtttgttcca | acctggtttg | gttgacgttg | aacaacctgg | cgtgggcgag   960 |
| ctgttattta | atactgtgca | atcggctgat | gttgatatca | gaagttccct | gtataaggcc  1020 |
| attgttcttt | caggtggttc | aagtatgtac | ccagggctgc | cttcgagatt | agagaaagaa  1080 |
| ttgaaacaat | tatggtttag | tagagtttta | cacaatgacc | cttcaagact | tgataaattc  1140 |
| aaagttagaa | ttgaagatcc | tccaaggaga | aagcatatgg | ttttcattgg | tggtgccgtt  1200 |
| ttagctagta | tcatggctga | taaagaccac | atgtggttgt | ctaagcaaga | atggcaagaa  1260 |
| agcgggccat | ctgcaatgac | taaatttggt | ccaagatag  | | 1299 |

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      PCR primer used to amplify yeast ORF prepared between
      univeral flanking sequences.

<400> SEQUENCE: 34
ggaattccag ctgaccacca tg                                                22

```
<210> SEQ ID NO 35
<211> LENGTH: 49
<212> TYPE: DNA
<213> ORGANISM: Artificial Sequence
<220> FEATURE:
<223> OTHER INFORMATION: Description of Artificial Sequence: Synthetic
      PCR primer used to amplify yeast ORF prepared between
      univeral flanking sequences.
<221> NAME/KEY: primer_bind
<222> LOCATION: (1)..(29)
<223> OTHER INFORMATION: T7 RNA polymerase recognition site to the PCR
      amplicon. Is the inition site for in vitro
      transcription of RNA.

<400> SEQUENCE: 35
tgaattgtaa tacgactcac tatagggagg atccccggga attgccatg                49

<210> SEQ ID NO 36
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-0413:  Probe derived from 39th ORF
      of the left arm of chromosome 6.  The ORF is on the
      Crick strand.  The probe starts at nucleotide 413.
      Probe is a portion of SEQ ID NO 31.
<300> PUBLICATION INFORMATION:
<302> TITLE: Analysis of the nucleotide sequence of chromosome VI
      from Saccharomyces cerevisiae
<303> JOURNAL: Nature Genet.
<304> VOLUME: 10
<306> PAGES: 261-268
<307> DATE: 1995

<400> SEQUENCE: 36
ccgttttgtc cttgtactct tccgg                                          25

<210> SEQ ID NO 37
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-HOM-25-0413:  Probe derived from real
      yeast ORF SEQ ID NO 36 that is homologous to other
      ORF derived sequences.  Source of homolog YKR097w
      at position 683.

<400> SEQUENCE: 37
acgttttaac tttgcactct tccgc                                          25

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      YFL039-DL12-24-0413: Synthetic probe similar to
      SEQ ID NO 36 except "DL" means deleted nucleotide
      T at feature location 12.

<400> SEQUENCE: 38
ccgttttgtc ctgtactctt ccgg                                           24

<210> SEQ ID NO 39
<211> LENGTH: 25
<212> TYPE: DNA
```

<213> ORGANISM: Artificial Sequence
<220> FEATURE:
<223> OTHER INFORMATION: Description of Artificial Sequence: Synthetic
    probe YFL039C-MM1012-25-0413 similar to SEQ ID NO
    36, except "MM" denotes nucleotide at position 12
    was changed to A.

<400> SEQUENCE: 39
ccgttttgtc catgtactct tccgg                                          25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:
    YFL039C-MM2012-25-0413 is a synthetic probe
    similar to SEQ ID NO 36, except nucleotide 12 is
    changed to G.

<400> SEQUENCE: 40
ccgttttgtc cgtgtactct tccgg                                          25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
    probe YFL039C-MM3012-25-0413 is similar to SEQ ID
    NO 36, except "MM" means nucleotide at position 12
    was changed to C.

<400> SEQUENCE: 41
ccgttttgtc cctgtactct tccgg                                          25

<210> SEQ ID NO 42
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-0461: is a probe derived from the
    39th ORF on the left arm of the chromosome 6. The ORF
    is on the Crick strand and the probe starts at
    nucleotide 461. Probe is a portion of SEQ ID NO
    31.
<300> PUBLICATION INFORMATION:
<302> TITLE: Analysis of the nucleotide sequence of chromosome VI
    from Saccharomyces cerevisiae
<303> JOURNAL: Nature Genet.
<304> VOLUME: 10
<306> PAGES: 261-268
<307> DATE: 1995

<400> SEQUENCE: 42
attccggtga tggtgttact cacgt                                          25

<210> SEQ ID NO 43
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-HOM-25-0461 is a probe derived from
    real yeast ORF SEQ ID NO 42 that is homologous to other
    ORF derived sequences. Source of homolog is
    YDL029W at position 470.

```
<400> SEQUENCE: 43
attccggtga cggtgttact catat                                              25

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence:
      YFL039C-DL12-24-0461 - Synthetic probe similar to
      SEQ ID NO 42 except nucleotide T at position 12 is
      deleted.

<400> SEQUENCE: 44
attccggtga tgtgttactc acgt                                               24

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM1012-25-0461 synthetic sequence similar
      to SEQ ID NO 42, except for changed nucleotide at
      position 12 to C.

<400> SEQUENCE: 45
attccggtga tcgtgttact cacgt                                              25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM2012-25-0461 synthetic probe similar to
      SEQ ID NO 42 except for changed nucleotide at
      position 12 to T.

<400> SEQUENCE: 46
attccggtga ttgtgttact cacgt                                              25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM3012-25-0461 is a synthetic probe
      similar to SEQ ID NO 42, except nucleotide 12 is
      changed to A.

<400> SEQUENCE: 47
attccggtga tagtgttact cacgt                                              25

<210> SEQ ID NO 48
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-0783 is a probe derived from the
      39th ORF on the left arm of chromosome 6. The ORF is
      on the Crick strand and the probe starts at
      nucleotide 783. Probe is a portion of SEQ ID NO
      31.
<300> PUBLICATION INFORMATION:
<302> TITLE: Analysis of the nucleotide sequence of chromosome VI
```

```
       from Saccharomyces cerevisiae
<303> JOURNAL: Nature Genet.
<304> VOLUME: 10
<306> PAGES: 261-268
<307> DATE: 1995

<400> SEQUENCE: 48
gttccatcct tctgttttgg gtttg                                            25

<210> SEQ ID NO 49
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-HOM-25-0783 is a probe derived from
      real yeast ORF SEQ ID NO 48 that is homologous to other
      ORF derived sequences.  Source of  homolog is
      YGL019W,  at position 79 in ORF.

<400> SEQUENCE: 49
attccatcgt tctgttccag atttg                                            25

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:
      YFL039C-DL12-24-0783 is a synthetic probe similar
      to  SEQ ID NO 48, except nucleotide C at position
      12 is deleted.

<400> SEQUENCE: 50
gttccatcct ttgttttggg tttg                                             24

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM1012-25-0783 is a synthetic probe
      similar to SEQ ID NO 48, except nucleotide at
      position 12 is changed to G.

<400> SEQUENCE: 51
gttccatcct tgtgttttgg gtttg                                            25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM2012-25-0783 is a synthetic probe
      similar to SEQ ID NO 48, except nucleotide at
      position 12 is changed to A.

<400> SEQUENCE: 52
gttccatcct tatgttttgg gtttg                                            25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence:
```

YFL039C-MM3012-25-0783 is a synthetic probe
similar to SEQ ID NO 48, except nucleotide at
position 12 is changed to T.

<400> SEQUENCE: 53
gttccatcct tttgttttgg gtttg                                          25

<210> SEQ ID NO 54
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-0955 is a probe derived from the
      39th ORF of the left arm of chromosome 6.  The ORF is
      on the Crick strand and the probe starts at
      nucleotide 955.  Probe is a portion of SEQ ID NO
      31.
<300> PUBLICATION INFORMATION:
<302> TITLE: Analysis of the nucleotide sequence of chromosome VI
      from Saccharomyces cerevisiae
<303> JOURNAL: Nature Genet.
<304> VOLUME: 10
<306> PAGES: 261-268
<307> DATE: 1995

<400> SEQUENCE: 54
gctttggctc catcttccat gaagg                                          25

<210> SEQ ID NO 55
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-HOM-25-0955 is a probe derived from
      real yeast ORF SEQ ID NO 54 that is homologous to other
      ORF-derived sequences.  The source of the  homolog
      probe is YCL028W at position 535 in ORF.

<400> SEQUENCE: 55
tctttggctt catctttcat gaatt                                          25

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:
      YFL039C-DL12-24-0955 is a synthetic probe similar
      to SEQ ID NO 54, except nucleotide A at position
      12 is deleted.

<400> SEQUENCE: 56
gctttggctc ctcttccatg aagg                                           24

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM1012-25-0955 is a sythetic probe similar
      to SEQ ID NO 54, except that nucleotide at
      position 12 is changed to T.

<400> SEQUENCE: 57
gctttggctc cttcttccat gaagg                                          25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence:
    YFL039C-MM2012-25-0955 is a synthetic probe
    similar to SEQ ID NO 54, except nucleotide at
    position 12 is changed to C.

<400> SEQUENCE: 58
gctttggctc cctcttccat gaagg                                    25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence:
    YFL039C-MM3012-25-0955 is a synthetic probe
    similar to SEQ ID NO 54, except nucleotide at
    position 12 is changed to G.

<400> SEQUENCE: 59
gctttggctc cgtcttccat gaagg                                    25

<210> SEQ ID NO 60
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-0983 is a probe derived from the
    39th ORF of the left arm of chromosome 6.  The ORF is
    on the Crick strand, and the probe starts at
    nucleotide 983.  Probe is a portion of SEQ ID NO
    31.
<300> PUBLICATION INFORMATION:
<302> TITLE: Analysis of the nucleotide sequence of chromosome VI
    from Saccharomyces cerevisiae
<303> JOURNAL: Nature Genet.
<304> VOLUME: 10
<306> PAGES: 261-268
<307> DATE: 1995

<400> SEQUENCE: 60
agatcattgc tcctccagaa agaaa                                    25

<210> SEQ ID NO 61
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-HOM-25-0983 is derived from real yeast
    ORF SEQ ID NO 60 that is homologous to other ORF
    derived sequences.  The source of the homolog is
    YHR129C starting at position 1013 of ORF.

<400> SEQUENCE: 61
agattatagc cccttcagaa agaaa                                25

<210> SEQ ID NO 62
<211> LENGTH: 24
<212> TYPE: DNA
<213> ORGANISM: Artificial Sequence
<220> FEATURE:

```
<223> OTHER INFORMATION: Description of Artificial Sequence:
      YFL039C-DL12-24-0983 is a synthetic probe similar
      to SEQ ID NO 60 except nucleotide C at position 12
      is deleted.

<400> SEQUENCE: 62
agatcattgc tctccagaaa gaaa                                          24

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM1012-25-0983 is a synthetic probe
      similar to SEQ ID NO 60, except nucleotide at
      position 12 is changed to G.

<400> SEQUENCE: 63
agatcattgc tgctccagaa agaaa                                         25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM2012-25-0983 is a synthetic probe
      similar to SEQ ID NO 60, except nucleotide at
      position 12 is changed to A.

<400> SEQUENCE: 64
agatcattgc tactccagaa agaaa                                         25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM3012-25-0983 is a synthetic probe
      similar to SEQ ID NO 60, except nucleotide at
      position 12 is changed to T.

<400> SEQUENCE: 65
agatcattgc ttctccagaa agaaa                                         25

<210> SEQ ID NO 66
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-25-1019 is a probe derived from the 39th
      ORF on the left arm of chromosome 6.  The ORF is
      on the Crick strand, and probe starts at
      nucleotide 1019.  Probe is a portion of SEQ ID NO
      31.
<300> PUBLICATION INFORMATION:
<302> TITLE: Analysis of the nucleotide sequence of chromosome VI
      from Saccharomyces cerevisiae
<303> JOURNAL: Nature Genet.
<304> VOLUME: 10
<306> PAGES: 261-268
<307> DATE: 1995

<400> SEQUENCE: 66
ggattggtgg ttctatcttg gcttc                                         25
```

```
<210> SEQ ID NO 67
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YFL039C-HOM-25-1019 is a probe derived from real
      yeast ORF SEQ ID NO 66 that is homologous to other
      ORF derived sequences.  The source homolog is
      YNR041C at position 544 in ORF.

<400> SEQUENCE: 67
ggaatgggcg ttctatcttt gcttc                                          25

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:
      YFL039C-DL12-24-1019 is a synthetic probe similar
      to SEQ ID NO 66, except nucleotide T at position
      12 is deleted.

<400> SEQUENCE: 68
ggattggtgg tctatcttgg cttc                                           24

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM1012-25-1019 is an synthetic probe
      similar to SEQ ID NO 66, except nucleotide at
      position 12 is changed to A.

<400> SEQUENCE: 69
ggattggtgg tactatcttg gcttc                                          25

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM2012-25-1019 is a synthetic probe
      similar to SEQ ID NO 66, except nucleotide at
      position 12 is changed to G.

<400> SEQUENCE: 70
ggattggtgg tgctatcttg gcttc                                          25

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence:
      YFL039C-MM3012-25-1019 is a synthetic probe
      similar to SEQ ID NO 66, except nucleotide at
      position 12 is changed to C.

<400> SEQUENCE: 71
ggattggtgg tcctatcttg gcttc                                          25

<210> SEQ ID NO 72
```

```
<211> LENGTH: 25
<212> TYPE: DNA
<213> ORGANISM: Artificial Sequence
<220> FEATURE:
<223> OTHER INFORMATION: Description of Artificial Sequence: A Cy3
      labeled sequence
<221> NAME/KEY: unsure
<222> LOCATION: (1)..(25)
<223> OTHER INFORMATION: Cy3 fluorophore label linked to 5'-OH via
      phosphodiester linkage

<400> SEQUENCE: 72
ggatacactg accagctacg atgat                                        25

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: A Cy5 labeled
      sequence
<221> NAME/KEY: unsure
<222> LOCATION: (1)..(25)
<223> OTHER INFORMATION: Cy5 fluorophore label linked to 5' -OH via
      phosphodiester linkage

<400> SEQUENCE: 73
ggatacactg accagctacg atgat                                        25

<210> SEQ ID NO 74
<211> LENGTH: 25
<212> TYPE: DNA
<213> ORGANISM: Saccharomyces cerevisiae
<220> FEATURE:
<221> NAME/KEY: source
<222> LOCATION: (1)..(25)
<223> OTHER INFORMATION: YHR129C-25-1049 is probe derived from the 129th
      ORF on the right arm of chromosome 8.  The ORF is
      on Crick strand and the probe starts at nucleotide
      1049.  Probe is a portion of SEQ ID NO 32.
<300> PUBLICATION INFORMATION:
<302> TITLE: Complete nucleotide sequence of Saccharomyces
      cerevisiae chromosome VIII
<303> JOURNAL: Science
<304> VOLUME: 265
<306> PAGES: 2077-2082
<307> DATE: 1994

<400> SEQUENCE: 74
ggattggtgg ttctatttta acggg                                              25

<210> SEQ ID NO 75
<211> LENGTH: 23
<212> TYPE: DNA
<213> ORGANISM: Saccharomyces cerevisiae
<220> FEATURE:
<221> NAME/KEY: source
<222> LOCATION: (1)..(23)
<223> OTHER INFORMATION: YPR040W-23-0290 is a probe derived from the
      omosome 16.  The ORF is on the Watson strand and the probe starts
      at nucleotide 290.
<300> PUBLICATION INFORMATION:
<302> TITLE: The nucleotide sequence of Saccharomyces cerevisiae
      chromosome XVI
<303> JOURNAL: Nature
<304> VOLUME: 387
<306> PAGES: 103-105
<307> DATE: 1997

<400> SEQUENCE: 75
ggaccatctc ctccagaaag aag                                                23
```

What is claimed is:

1. A method for selecting a set of target-specific oligonucleotide probes for use in analyzing a target nucleic acid sequence, said method comprising:
   (a) identifying a cross-hybridization oligonucleotide probe based on a candidate target-specific oligonucleotide probe for said target nucleic acid sequence wherein said cross-hybridization oligonucleotide probe measures the extent of occurrence of a cross-hybridization event, having a predetermined probability, to an interfering nucleic acid sequence,
   (b) determining cross-hybridization results employing said cross-hybridization oligonucleotide probe and said target-specific oligonucleotide probe wherein said cross-hybridization results are determined by a hybridization study of a sample suspected of containing a target nucleic acid sequence using said target-specific oligonucleotide probe and said cross-hybridization probe and
   (c) selecting or rejecting said target-specific oligonucleotide probe for said set of target specific oligonucleotide probes based on said cross-hybridization results.

2. A method according to claim 1 wherein said cross-hybridization oligonucleotide probe is a single probe obtained from a homology algorithm.

3. A method according to claim 1 wherein said cross-hybridization probe is part of a set of oligonucleotide probes wherein the cross-hybridization result obtained with said set of oligonucleotide probes measures the extent of occurrence of hybridization events that have a predetermined probability.

4. The method of claim 1 wherein steps (a)–(c) are repeated.

5. A method according to claim 1 wherein said identifying of a cross-hybridization oligonucleotide probe in step (a) is carried out by a process comprising determining homologous sequences to target genes that meet predetermined criteria with respect to said oligonucleotide probe specific for said target nucleic acid sequence.

6. A method according to claim 5 wherein said criteria comprise a predetermined number of mismatches between said target-specific oligonucleotide probe and said cross-hybridization oligonucleotide probe derived from said homologous sequences.

7. A method according to claim 5 wherein said criteria comprise a distribution of mismatches between said target-specific oligonucleotide probe and said probe derived from said homologous sequences.

8. A method according to claim 5 wherein said criteria comprise accepting or rejecting said homologous sequences on the basis of a predicted free energy compared to a predetermined predicted free energy of the hybridizing of said target-specific oligonucleotide probe with said target nucleic acid sequence.

9. A method according to claim 1 wherein said identifying of step (a) is carried out by a process comprising incorporating a selected combination of possible nucleotide substitutions at one or more positions in a single cross-hybridization oligonucleotide probe.

10. A method according to claim 9 wherein said identifying of step (a) is carried out by a process comprising deleting nucleotides at one or more positions in a single cross-hybridization oligonucleotide probe.

11. A method according to claim 9 wherein said identifying of step (a) is carried out by a process comprising inserting nucleotides at one or more positions in a single cross-hybridization oligonucleotide probe.

12. A method for selecting a set of target-specific oligonucleotide probes for use in analyzing a target nucleic acid sequence, said method comprising:
   (a) identifying a cross-hybridization oligonucleotide probe based on said target nucleic acid sequence by a process comprising determining homologous sequences in target genes that meet predetermined criteria with respect to said oligonucleotide probe specific for said target nucleic acid sequence,
   (b) determining cross-hybridization results employing said cross-hybridization oligonucleotide probe and target-specific oligonucleotide probe wherein said cross-hybridization results are determined by a hybridization study of a sample suspected of containing a target nucleic acid sequence using said target-specific oligonucleotide probe and said cross-hybridization probe and
   (c) selecting or rejecting said target-specific oligonucleotide probe for said set based on said cross-hybridization results.

13. A method according to claim 12 wherein said criteria comprise a predetermined number of mismatches between said target-specific oligonucleotide probe and said probe derived from said homologous sequences.

14. A method according to claim 12 wherein said criteria comprise a distribution of mismatches between said target-specific oligonucleotide probe and said probe derived from said homologous sequences.

15. A method according to claim 12 wherein said criteria comprise homologous sequences having a predicted free energy substantially the same as a predetermined predicted free energy of the hybridizing of said target-specific oligonucleotide probe with said target nucleic acid sequence.

16. A method for selecting a set of target-specific oligonucleotide probes for use in analyzing a target nucleic acid sequence, said method comprising:
   (a) identifying a cross-hybridization oligonucleotide probe based on said target nucleic acid sequence by a process comprising incorporating a selected combination of possible nucleotide substitutions at one or more positions in a single cross-hybridization oligonucleotide probe,
   (b) determining cross-hybridization results employing said cross-hybridization oligonucleotide probe and target-specific oligonucleotide probe and
   (c) selecting or rejecting said target-specific oligonucleotide probe for said set based on said cross-hybridization results.

17. A method for selecting a set of target-specific oligonucleotide probes for use in analyzing a target nucleic acid sequence, said method comprising:
   (a) identifying a cross-hybridization oligonucleotide probe based on said target nucleic acid sequence by a process comprising deleting nucleotides at one or more positions in a single cross-hybridization oligonucleotide probe,
   (b) determining cross-hybridization results employing said cross-hybridization oligonucleotide probe and target-specific oligonucleotide probe and
   (c) selecting or rejecting said target-specific oligonucleotide probe for said set based on said cross-hybridization results.

18. A method for selecting a set of target-specific oligonucleotide probes for use in analyzing a target nucleic acid sequence, said method comprising:
   (a) identifying a cross-hybridization oligonucleotide probe based on said target nucleic acid sequence by a process comprising inserting nucleotides at one or more positions in a single cross-hybridization oligonucleotide probe, (b) determining cross-hybridization results employing said cross-hybridization oligonucleotide probe and target-specific oligonucleotide probe and (c) selecting or rejecting said target-specific oligonucleotide probe for said set based on said cross-hybridization results.

19. A kit for analyzing a target nucleic acid sequence, said kit comprising in packaged combination:

(a) an oligonucleotide probe specific for said target nucleic acid sequence, (b) a set of cross-hybridization oligonucleotide probes based on said target nucleic acid sequence wherein cross-hybridization results obtained with said set measures the extent of the occurrence of cross-hybridization events, having a predetermined probability, between an interfering nucleic acid sequence and said oligonucleotide probe specific for said target nucleic sequence and wherein said predetermined probability is a threshold level based on information about said target nucleic acid sequence and said oligonucleotide specific for a target nucleic acid sequence, (c) a written description of a method according to claim 1.

20. A kit according to claim 19 wherein said set of cross-hybridization oligonucleotide probes is obtained from a homology algorithm.

21. A kit according to claim 19 wherein said target-specific oligonucleotide probe comprises a label.

22. A kit according to claim 19 wherein said target-specific oligonucleotide probe is bound to a support.

23. A kit according to claim 22 wherein said support comprises an array of different target-specific oligonucleotide probes.

24. A computer based method for selecting a set of target-specific oligonucleotide probes for use in analyzing a target nucleic acid sequence, said method comprising:

(a) identifying under computer control a cross-hybridization oligonucleotide probe based on said target nucleic acid sequence wherein said cross-hybridization oligonucleotide probe measures the extent of the occurrence of a cross-hybridization event, having a predetermined probability, to an interfering nucleic acid sequence, (b) determining under computer control cross-hybridization results employing said cross-hybridization oligonucleotide probe and target-specific oligonucleotide probe wherein said cross-hybridization results are determined by a hybridization study of a sample suspected of containing a target nucleic acid sequence using said target-specific oligonucleotide probe and said cross-hybridization probe and (c) selecting or rejecting under computer control said target-specific oligonucleotide probe for said set of target specific oligonucleotide probes based on said cross-hybridization results.

25. A computer system for selecting a set of target-specific oligonucleotide probes for use in analyzing a target nucleic acid sequence, said system comprising:

(a) input means for introducing a target nucleotide sequence into said computer system, (b) means for determining a cross-hybridization oligonucleotide probe based on said target nucleic acid sequence wherein said cross-hybridization oligonucleotide probe measures the extent of the occurrence of a cross-hybridization event, having a predetermined probability, to an interfering nucleic acid sequence wherein said cross-hybridization results are determined by a hybridization study of a sample suspected of containing a target nucleic acid sequence using said target-specific oligonucleotide probe and said cross-hybridization probe, (c) memory means for determining cross-hybridization results employing said cross-hybridization oligonucleotide probe and target-specific oligonucleotide probe, (d) means for storing said cross-hybridization results, (e) means for controlling said computer system to select or reject said target-specific oligonucleotide probe for said set of target specific oligonucleotide probes based on said cross-hybridization results, (f) means for storing selection results from step (e), and (g) means for outputting data relating to said selection results.

26. A computer program product comprising a computer readable storage medium having a computer program stored thereon which, when loaded into a computer, selects a set of target-specific oligonucleotide probes for use in analyzing a target nucleic acid sequence by performing steps comprising:

(a) identifying under computer control a cross-hybridization oligonucleotide probe based on said target nucleic acid sequence wherein said cross-hybridization oligonucleotide probe measures the extent of the occurrence of a cross-hybridization event, having a predetermined probability, to an interfering nucleic acid sequence, (b) determining under computer control cross-hybridization results employing said cross-hybridization oligonucleotide probe and target-specific oligonucleotide probe wherein said cross-hybridization results are determined by a hybridization study of a sample suspected of containing a target nucleic acid sequence using said target-specific oligonucleotide probe and said cross-hybridization probe and (c) selecting or rejecting under computer control said target-specific oligonucleotide probe for said set of target specific oligonucleotide probes based on said cross-hybridization results.

27. A computer program product according to claim 26 wherein said identifying of step (a) is carried out by a process comprising determining homologous sequences in target genes that meet predetermined criteria with respect to said oligonucleotide probe specific for said target nucleic acid sequence.

28. A computer program product according to claim 27 wherein said criteria comprise a predetermined number of mismatches between said target-specific oligonucleotide probe and said cross-hybridization oligonucleotide probe derived from said homologous sequences.

* * * * *